(12) United States Patent
Tsourkas et al.

(10) Patent No.: US 11,913,026 B2
(45) Date of Patent: Feb. 27, 2024

(54) BISPECIFIC CYTOTOXIC LYMPHOCYTE OR MACROPHAGE-REDIRECTING AUTOANTIBODIES, METHODS FOR PRODUCTION THEREOF AND METHODS OF TREATMENT

(71) Applicant: THE TRUSTEES OF THE UNIVERSITY OF PENNSYLVANIA, Philadelphia, PA (US)

(72) Inventors: Andrew Tsourkas, Bryn Mawr, PA (US); James Z. Hui, Philadelphia, PA (US); Burcin Altun, Philadelphia, PA (US); Fabiana Zappala, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 614 days.

(21) Appl. No.: 16/821,933

(22) Filed: Mar. 17, 2020

(65) Prior Publication Data
US 2020/0299646 A1    Sep. 24, 2020

Related U.S. Application Data

(60) Provisional application No. 62/820,157, filed on Mar. 18, 2019.

(51) Int. Cl.
| | |
|---|---|
| *C12N 5/00* | (2006.01) |
| *A61P 35/00* | (2006.01) |
| *C07K 16/28* | (2006.01) |
| *C07K 16/30* | (2006.01) |
| *C12N 5/0783* | (2010.01) |
| *A61K 39/00* | (2006.01) |

(52) U.S. Cl.
CPC ............ *C12N 5/0638* (2013.01); *A61P 35/00* (2018.01); *C07K 16/2809* (2013.01); *C07K 16/2827* (2013.01); *C07K 16/3015* (2013.01); *A61K 2039/507* (2013.01); *C07K 2317/622* (2013.01); *C12N 2510/00* (2013.01)

(58) Field of Classification Search
CPC ... C12N 5/0638; C12N 2510/00; A61P 35/00; C07K 16/2809; C07K 16/2827; C07K 16/3015; C07K 2317/622; C07K 16/2863; C07K 16/30; C07K 2317/73; C07K 2317/90; C07K 2317/92; A61K 2039/507; A61K 39/395; A61K 2039/505
See application file for complete search history.

(56) References Cited

U.S. PATENT DOCUMENTS 5,780,033 A * 7/1998 Torchilin ................ A61P 43/00
530/389.7

FOREIGN PATENT DOCUMENTS

| WO | WO 2016/183387 | * 11/2016 | ............ A61K 47/48 |
|---|---|---|---|
| WO | WO 2018/071777 | * 4/2018 | ............ A61K 39/39 |

OTHER PUBLICATIONS

Aldous et al. (Bioorganic and Medicinal Chemistry, 26: 2842-2849, 2018).*
Wang et al. (Cell Research, 27: 11-13, 2017).*
Abt et al. "Evaluation of lung metastasis in mouse mammary tumor models by quantitative real-time PCR." Journal of visualized experiments: JoVE 107 (2016), pp. 1-14.
Baselga et al. "Lapatinib with trastuzumab for HER2-positive early breast cancer (NeoALTTO): a randomised, open-label, multicentre, phase 3 trial." The Lancet 379.9816 (2012): 633-640.
Bencherif et al. "Injectable cryogel-based whole-cell cancer vaccines." Nature communications 6.1 (2015): 1-13.
Blank et al. "Blockade of PD-L1 (B7-H1) augments human tumor-specific T cell responses in vitro." International journal of cancer 119.2 (2006): 317-327.
Bluemel et al. "Epitope distance to the target cell membrane and antigen size determine the potency of T cell-mediated lysis by BITE antibodies specific for a large melanoma surface antigen." Cancer immunology, immunotherapy 59.8 (2010): 1197-1209. (Abstract).
Boxer., et al. "Isoform-specific requirement for Akt1 in the developmental regulation of cellular metabolism during lactation." Cell metabolism 4.6 (2006): 475-490.
Cai et al. "scFv-based "grababody" as a general strategy to improve recruitment of immune effector cells to antibody-targeted tumors." Cancer research 73.8 (2013): 2619-2627.
Chatenoud et al. "CD3-specific antibodies: a portal to the treatment of autoimmunity." Nature Reviews Immunology 7.8 (2007): 622-632.
Chin et al. "Addition of a photocrosslinking amino acid to the genetic code of *Escherichia coli*." Proceedings of the National Academy of Sciences 99.17 (2002): 11020-11024.
Christ et al. "Repertoires of aggregation-resistant human antibody domains." Protein Engineering, Design & Selection 20.8 (2007): 413-416.
D'Cruz et al. "c-MYC induces mammary tumorigenesis by means of a preferred pathway involving spontaneous Kras2 mutations." Nature medicine 7.2 (2001): 235-239.
De Groot et al. "Prediction of immunogenicity for therapeutic proteins: state of the art." Current Opinion in Drug Discovery and Development 10.3 (2007): 332.
De Gruijl et al. "Whole-cell cancer vaccination: from autologous to allogeneic tumor-and dendritic cell-based vaccines." Cancer Immunology, Immunotherapy 57.10 (2008): 1569.

(Continued)

*Primary Examiner* — Nelson B Moseley, II
(74) *Attorney, Agent, or Firm* — Mark S. Cohen; PEARL COHEN ZEDEK LATZER BARATZ LLP

(57) ABSTRACT

A bispecific cytotoxic lymphocyte or macrophage-redirecting autoantibody comprising a cytotoxic lymphocyte or macrophage targeting domain and an autoantibody. Methods for producing bispecific cytotoxic lymphocyte or macrophage-redirecting autoantibody comprising a cytotoxic lymphocyte or macrophage targeting domain and an autoantibody. Methods for treating a subject in need thereof comprising administering to the subject an isolated bispecific cytotoxic lymphocyte or macrophage-redirecting autoantibody.

26 Claims, 10 Drawing Sheets
Specification includes a Sequence Listing.

(56) References Cited

OTHER PUBLICATIONS

Derrick et al. "Crystal structure of a *Streptococcal* protein G domain bound to an Fab fragment." Nature 359.6397 (1992): 752-754. (Abstract).

Dima et al. "Effect of protein A and its fragment B on the catabolic and Fc receptor sites of IgG." European journal of immunology 13.8 (1983): 605-614. (Abstract).

Donehower et al. "Deficiency of p53 accelerates mammary tumorigenesis in Wnt-1 transgenic mice and promotes chromosomal instability." Genes & development 9.7 (1995): 882-895.

Dorman et al. "Benzophenone photophores in biochemistry." Biochemistry 33.19 (1994): 5661-5673.

Doyle et al. "Long-term results of local recurrence after breast conservation treatment for invasive breast cancer." International Journal of Radiation Oncology* Biology* Physics 51.1 (2001): 74-80.

Dranoff et al. "Vaccination with irradiated tumor cells engineered to secrete murine granulocyte-macrophage colony-stimulating factor stimulates potent, specific, and long-lasting anti-tumor immunity." Proceedings of the National Academy of Sciences 90.8 (1993): 3539-3543.

Famm et al. "Thermodynamically stable aggregation-resistant antibody domains through directed evolution." Journal of molecular biology 376.4 (2007): 926-931. (Abstract).

Fiandra et al. "Assessing the in vivo targeting efficiency of multifunctional nanoconstructs bearing antibody-derived ligands." Acs Nano 7.7 (2013): 6092-6102.

Fisher et al. "Significance of ipsilateral breast tumour recurrence after lumpectomy. Lancet". 1991;338(8763):327-31. (Abstract).

Fitzgerald et al., "MM-141, an IGF-IR- and ErbB3-Directed Bispecific Antibody, Overcomes Network Adaptations That Limit Activity of IGF-IR Inhibitors." Molecular Cancer Therapeutics, 13(2) Feb. 2014, pp. 410-425.

Fortin et al. "Local failure is responsible for the decrease in survival for patients with breast cancer treated with conservative surgery and postoperative radiotherapy." Journal of clinical oncology 17.1 (1999): 101-101. (Abstract).

Gall et al. "T cells armed with anti-CD3x anti-CD20 bispecific antibody enhance killing of CD20+ malignant B cells and bypass complement-mediated rituximab resistance in vitro." *Experimental hematology* 33.4 (2005): 452-459. (Abstract).

Gunther et al. "A novel doxycycline-inducible system for the transgenic analysis of mammary gland biology." The FASEB Journal 16.3 (2002): 283-292.

Gunther et al. "Impact of p53 loss on reversal and recurrence of conditional Wnt-induced tumorigenesis." Genes & development 17.4 (2003): 488-501.

Hernandez-Hoyos, et al. "MOR209/ES414, a novel bispecific antibody targeting PSMA for the treatment of metastatic castration-resistant prostate cancer." *Molecular cancer therapeutics* 15.9 (2016): 2155-2165.

Hmila et al. "VHH, bivalent domains and chimeric heavy chain-only antibodies with high neutralizing efficacy for scorpion toxin Aahl'." Molecular immunology 45.14 (2008): 3847-3856.

Ho et al. "Biologic activity of irradiated, autologous, GM-CSF-secreting leukemia cell vaccines early after allogeneic stem cell transplantation." Proceedings of the National Academy of Sciences 106.37 (2009): 15825-15830.

Hollander et al. "Selection of reaction additives used in the preparation of monomeric antibody—calicheamicin conjugates." Bioconjugate chemistry 19.1 (2007): 358-361. (Abstract).

Hu et al. "Towards personalized, tumour-specific, therapeutic vaccines for cancer." Nature Reviews Immunology 18.3 (2017): 168-182.

Hui et al. "Facile Method for the Site-Specific, Covalent Attachment of Full-Length IgG onto Nanoparticles." Small 10.16 (2014): 3354-3363.

Hui et al. "LASIC: Light activated site-specific conjugation of native IgGs." Bioconjugate chemistry 26.8 (2015): 1456-1460.

Hui et al. "Optimization of photoactive protein Z for fast and efficient site-specific conjugation of native IgG." Bioconjugate chemistry 25.9 (2014): 1709-1719.

Jacobs et al. "Cross-interaction chromatography: a rapid method to identify highly soluble monoclonal antibody candidates." Pharmaceutical research 27.1 (2010): 65-71.

Jacobs et al. "Efficiency of T cell triggering by anti-CD3 monoclonal antibodies (mAb) with potential usefulness in bispecific mAb generation." Cancer Immunology, Immunotherapy 44.5 (1997): 257-264.

Jaffee et al. "Novel allogeneic granulocyte-macrophage colony-stimulating factor-secreting tumor vaccine for pancreatic cancer: a phase I trial of safety and immune activation." J Clin Oncol. 2001;19(1):145-56. (Abstract).

Jang et al. "Isoform-specific ras activation and oncogene dependence during MYC-and Wnt-induced mammary tumorigenesis." Molecular and cellular biology 26.21 (2006): 8109-8121.

Jawa et al. "T-cell dependent immunogenicity of protein therapeutics: preclinical assessment and mitigation." Clinical immunology 149.3 (2013): 534-555.

Keenan et al. "Whole cell vaccines past progress and future strategies." Seminars in oncology. vol. 39. No. 3. WB Saunders, 2012, pp. 276-286.

Le Gall et al. "Effect of linker sequences between the antibody variable domains on the formation, stability and biological activity of a bispecific tandem diabody." Protein Engineering Design and Selection 17.4 (2004): 357-366.

Lenoff et al. "Hydrophobic interaction chromatography of proteins: I. The effects of protein and adsorbent properties on retention and recovery." Journal of Chromatography A 1141.2 (2007): 191-205. (Abstract).

Lienqueo et al. "New approaches for predicting protein retention time in hydrophobic interaction chromatography." Journal of Molecular Recognition: An Interdisciplinary Journal 19.4 (2006): 260-269.

Liu et al. "Genetic incorporation of unnatural amino acids into proteins in mammalian cells." Nature methods 4.3 (2007): 239-244.

Lu et al. "Tetravalent anti-CD20/CD3 bispecific antibody for the treatment of B cell lymphoma." Biochemical and biophysical research communications 473.4 (2016): 808-813. (Abstract).

Lutterbuese et al. "T cell-engaging BiTE antibodies specific for EGFR potently eliminate KRAS-and BRAF-mutated colorectal cancer cells." Proceedings of the National Academy of Sciences 107.28 (2010): 12605-12610.

Mack et al. "A small bispecific antibody construct expressed as a functional single-chain molecule with high tumor cell cytotoxicity." Proceedings of the National Academy of Sciences 92.15 (1995): 7021-7025.

Meyer et al. "Single-site mutations in a hyperthermophilic variant of the B1 domain of protein G result in self-assembled oligomers." Biochemistry 44.7 (2005): 2360-2368. (Abstract).

Moody et al. "Conditional activation of Neu in the mammary epithelium of transgenic mice results in reversible pulmonary metastasis." Cancer cell 2.6 (2002): 451-461.

Moore et al. "A novel bispecific antibody format enables simultaneous bivalent and monovalent co-engagement of distinct target antigens." MAbs. vol. 3. No. 6. Taylor & Francis, 2011.

NCT01773395—ClinicalTrials.gov.
NCT02106091—ClinicalTrials.gov.
NCT02262910—ClinicalTrials.gov.

Perruche et al. "Lethal effect of CD3-specific antibody in mice deficient in TGF-β1 by uncontrolled flu-like syndrome." The Journal of Immunology 183.2 (2009): 953-961.

Raghu et al., "SAR156597 in idiopathic pulmonary fibrosis: a phase 2 placebo-controlled study (DRI11772)." European Respiratory Journal 2018 52: 1801130; pp. 1-12.

Rich et al. "Endogenous antibodies for tumor detection." Scientific reports 4 (2014): 5088.

Robidoux et al. "Lapatinib as a component of neoadjuvant therapy for HER2-positive operable breast cancer (NSABP protocol B-41): an open-label, randomised phase 3 trial." The Lancet Oncology 14.12 (2013): 1183-1192. (Abstract).

Roopenian et al., "FcRn: the neonatal Fc receptor comes of age." Nature reviews immunology 7.9 (2007): 715-725.

(56) References Cited

OTHER PUBLICATIONS

Root et al. "Development of PF-06671008, a highly potent anti-P-cadherin/anti-CD3 bispecific DART molecule with extended half-life for the treatment of cancer." Antibodies 5.1 (2016): 6.
Rosenberg, A. "A risk-based approach to immunogenicity concerns of therapeutic protein products, Part 1: considering host-specific and product-specific factors impacting immunogenicity." Biopharm Intl (2004); 19:22-6.
Rosenberg, A. "A risk-based approach to immunogenicity concerns of therapeutic protein products. Part 2: considering host-specific and product-specific factors impacting immunogenicity." Biopharm Intl (2004):19:34-42.
Salazar-Fontana et al. "Approaches to mitigate the unwanted immunogenicity of therapeutic proteins during drug development." The AAPS journal 19.2 (2017): 377-385. (Abstract).
Salmerón et al. "A conformational epitope expressed upon association of CD3-epsilon with either CD3-delta or CD3-gamma is the main target for recognition by anti-CD3 monoclonal antibodies." The Journal of Immunology 147.9 (1991): 3047-3052.
Sarkisian et al. "Dose-dependent oncogene-induced senescence in vivo and its evasion during mammary tumorigenesis." Nature cell biology 9.5 (2007): 493-505.
Schmoor et al. "Role of isolated locoregional recurrence of breast cancer: results of four prospective studies." *Journal of Clinical Oncology* 18.8 (2000): 1696-1708. (Abstract).
Slamon et al. "Human breast cancer: correlation of relapse and survival with amplification of the HER-2/neu oncogene." science 235.4785 (1987): 177-182.
Slamon et al. "Studies of the HER-2/neu proto-oncogene in human breast and ovarian cancer." Science 244.4905 (1989): 707-712.
Sörensen et al. "First-in-human molecular imaging of HER2 expression in breast cancer metastases using the 111In-ABY-025 affibody molecule." Journal of nuclear medicine 55.5 (2014): 730-735.

Stanglmaier et al. "Bi20 (fBTA05), a novel trifunctional bispecific antibody (anti-CD20x anti-CD3), mediates efficient killing of B-cell lymphoma cells even with very low CD20 expression levels." International journal of cancer 123.5 (2008): 1181-1189.
Stebbings et al. "Safety of biologics, lessons learnt from TGN1412." Current opinion in biotechnology 20.6 (2009): 673-677.
Sulica et al. "Effect of protein A of *Staphylococcus aureus* on the binding of monomeric and polymeric IgG to Fc receptor-bearing cells." Immunology 38.1 (1979): 173.
Sun et al. "Anti-CD20/CD3 T cell-dependent bispecific antibody for the treatment of B cell malignancies." Science translational medicine 7.287 (2015): 287ra70-287ra70.
Taki et al. "A novel bispecific antibody against human CD3 and ephrin receptor A10 for breast cancer therapy." PloS one 10.12 (2015): e0144712.
Wakankar et al. "Physicochemical stability of the antibody-drug conjugate trastuzumab-DM1: changes due to modification and conjugation processes." Bioconjugate chemistry 21.9 (2010): 1588-1595. (Abstract).
Wang et al. "Proximity-Based Sortase-Mediated Ligation." Angewandte Chemie International Edition 56.19 (2017): 5349-5352.
Wu et al. "Site-specific chemical modification of recombinant proteins produced in mammalian cells by using the genetically encoded aldehyde tag." Proceedings of the National Academy of Sciences 106.9 (2009): 3000-3005.
Xia et al. "Whole-cell cancer vaccines induce large antibody responses to carbohydrates and glycoproteins." Cell chemical biology 23.12 (2016): 1515-1525.
Young et al. "An enhanced system for unnatural amino acid mutagenesis in *E. coli*." Journal of molecular biology 395.2 (2010): 361-374.

\* cited by examiner

BISPECIFIC CYTOTOXIC LYMPHOCYTE OR MACROPHAGE-REDIRECTING AUTOANTIBODIES, METHODS FOR PRODUCTION THEREOF AND METHODS OF TREATMENT

GOVERNMENT INTEREST STATEMENT

This invention was supported by Grant Numbers R21CA187657 and R21EB018863 from the National Institutes of Health. The United States government has certain rights in the invention.

FIELD OF THE INVENTION

This invention relates to bispecific cytotoxic lymphocyte or macrophage-redirecting autoantibodies and methods for producing such bispecific autoantibodies by conjugating cytotoxic lymphocyte or macrophage targeting domains to a living subject's own autoantibodies. This invention also relates to methods for treating a patient in need thereof comprising administering to the subject cytotoxic lymphocyte or macrophage redirecting autoantibodies.

BACKGROUND OF THE INVENTION

It has long been recognized that tumor cells express tumor-specific antigens that can be utilized as targets for immunotherapies. Conventional immunotherapies seek to stimulate or reinforce the T cell response against these tumor antigens. One such approach is adoptive cell transfer (ACT), which involves expanding a patient's own immune cells (with or without genetic modification) to enhance the immune response. It has been demonstrated that ACT can lead to the complete eradication of cancer in some patients. Despite the encouraging therapeutic results, the efficacy of ACT can be limited in many cases, due to the heterogeneity of antigen expression and/or the loss of cell surface antigen expression during disease progression. Moreover, immune checkpoint molecules can severely suppress the cytolytic potency of T cell-based therapies.

In contrast to stimulating the immune response to treat cancer, an alternative therapeutic approach involves using immune checkpoint inhibitors to prevent the tumor microenvironment from suppressing the native immune response. Recent clinical trials have demonstrated that immune checkpoint blockade can lead to a durable tumor response; however, this effect is only seen in a minority of treated patients. Efficacy seems to be correlated with the mutational landscape, with tumors that possess many mutations being more likely to respond to this form of treatment. Since tumors with more mutations are likely to trigger a stronger T cell response, these findings suggest that tumors that do not respond to immune checkpoint blockade would benefit from immunotherapies that stimulate the T cell response. This has led to the exploration of treatments that combine ACT and checkpoint inhibitors. While initial results have been promising, many of the same limitations faced by ACT as a stand alone therapeutic are likely to still exist.

Given the inadequacies of current immunotherapies, there exists a vital need for improved compositions and therapeutically effective methods for treating tumors.

SUMMARY OF THE INVENTION

In one aspect, this invention provides a bispecific cytotoxic lymphocyte or macrophage-redirecting autoantibody comprising a cytotoxic lymphocyte or macrophage targeting domain and an autoantibody. In an embodiment, the cytotoxic lymphocyte is a T cell or natural killer cell. In an embodiment, the autoantibody is an IgG molecule that is isolated from a patient and is against a tumor, autoantigen, or foreign body, wherein the foreign body is a virus, bacteria, or parasite. In an embodiment, the cytotoxic lymphocyte or macrophage targeting domain is an antibody or an antibody fragment, wherein the antibody is Immunoglobulin G (IgG) and the antibody fragment is an Fc, a single chain Fv (scFv), an Fab, Fab', Fv, F(ab')$_2$, affibody, nanobody, single domain antibody, monobody, anticalin, DARPin, Centyrin, Knottin, variant thereof. In an embodiment, the cytotoxic lymphocyte or macrophage targeting domain is fused to a photoreactive antibody-binding domain (pAbBD), wherein the pAbBD contains a photoreactive crosslinker that is photoreactively conjugated to an autoantibody isolated from a living subject.

In another aspect, this invention provides a method for producing a bispecific cytotoxic lymphocyte or macrophage-redirecting autoantibody, comprising: isolating an endogenous autoantibody from sera of a living subject having a tumor or foreign body; covalently conjugating the isolated endogenous autoantibody to a cytotoxic lymphocyte or macrophage targeting domain, wherein the cytotoxic lymphocyte or macrophage targeting domain is fused to a photoreactive antibody-binding domain (pAbBD), and the pAbBD contains a photoreactive crosslinker, that upon irradiating with long wavelength UV light covalently links the pAbBD and the cytotoxic lymphocyte or macrophage targeting domain to the isolated endogenous autoantibody, thereby producing the bispecific cytotoxic lymphocyte or macrophage-redirecting autoantibody.

In a further aspect, this invention provides a method for treating a subject in need thereof comprising administering to the subject an isolated bispecific cytotoxic lymphocyte or macrophage-redirecting autoantibody comprising a cytotoxic lymphocyte or macrophage targeting domain photoreactively conjugated to an autoantibody of a living subject, wherein the antibody-binding domain comprises a photoreactive crosslinker. In some embodiments, the subject has cancer. In certain embodiments, the subject has breast cancer. In various embodiments, the subject has a virus, bacterial, or parasite infection.

Other features and advantages of this invention will become apparent from the following detailed description, examples and figures. It should be understood, however, that the detailed description and the specific examples while indicating certain embodiments of the invention are given by way of illustration only, since various changes and modifications within the spirit and scope of the invention will become apparent to one skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 6A shows dose-dependent binding of photo-crosslinked anti-Her2 (Trastuzumab)×anti-CD3 (OKT3) BAb and unconjugated Trastuzumab to Her2-positive breast cancer cells. FIG. 6B shows binding of a photo-crosslinked anti-Her2×anti-CD3 Bab, unconjugated OKT3, and anti-CD3 scFv (OKT3) to CD3-positive T cells. FIG. 6C shows dose-dependent binding of photo-crosslinked anti-EGFR (Cetuximab)×anti-CD3 nanobody BAb and unconjugated Cetuximab to EGFR-positive breast cancer cells (MDA-468-MB).

(FIG. 9A) Schematic of proximity-based sortase ligation (PBSL). Two binding partners are used to bring the sortase recognition motif (LPXTG) into close proximity with sortase, to increase the efficiency of ligation between the pAbBD-scFv and any peptide that possesses an N-terminal glycine. The peptide can be labeled with any chemical moiety, e.g. fluorophore, biotin, etc. (red star). (FIG. 9B) When SpyCatcher and SpyTag are employed as binding domains, ~80% of the expressed recombinant protein is captured. (FIG. 9C) The efficiency of ligation is >95% in the PBSL system and is completed in ~4 hrs.

FIG. 10A shows T cell-mediated cytolysis of EGFR-positive MDA-468-MB tumor cells 12 hrs post-treatment with Cetuximab photocrosslinked with pAbBD-anti-CD3 scFv (squares) or pAbBD-anti-CD3 nanobody (circles) fusion proteins, Cetuximab mixed with free anti-CD3 nanobody (upwards triangle), and Rituximab conjugated with anti-CD3 nanobody (downwards triangle). All assays were performed with enriched T cells at a 10:1 effector-to-target ratio. FIG. 10B shows effector-to-target ratio optimization of T cell mediated cytolysis 12 hrs post-treatment with 1 nM anti-CD3 nanobody modified Cetuximab and Cetexuimab mixed with free anti-CD3 nanobody. FIG. 10C shows cytolysis kinetics of Cetuximab photocrosslinked with anti-CD3 nanobody using 10:1 effector-to-target ratio.

DETAILED DESCRIPTION OF THE INVENTION

Figure 1:
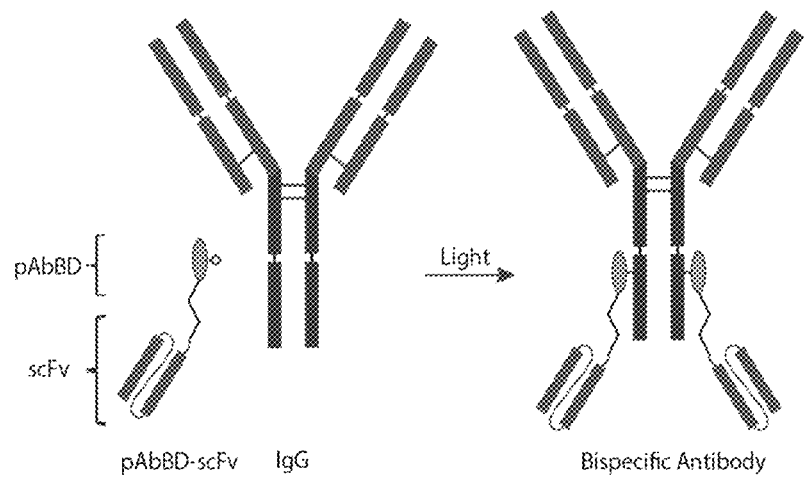
FIG. 1. Schematic describing method for rapid production of a bispecific antibody (Bab). An anti-CD3 scFv is fused to a photoreactive antibody-binding domain (pAbBD). Irradiation with non-damaging long-wavelength UV light allows for covalent attachment of the fusion protein to the Fc-region of IgG.

The present invention may be understood more readily by reference to the following detailed description which forms a part of this disclosure. It is to be understood that this invention is not limited to the specific methods, products, conditions or parameters described and/or shown herein, and that the terminology used herein is for the purpose of describing particular embodiments by way of example only and is not intended to be limiting of the claimed invention.

The goal of immunotherapy in cancer treatment is to enhance the immune system's natural ability to detect and kill cancer cells. This can be achieved by either (i) stimulating or reinforcing the hosts immune response to cancer or (ii) weakening immunosuppressive conditions within a tumor. Several approaches that have been developed to boost the host immune response include peptide vaccines, dendritic cell vaccines, and adoptive cells transfer (ACT). ACT has recently garnered a great deal of interest because of its success in eradicating some very advanced cancers, primarily melanoma, leukemia and lymphoma, in some patients. ACT uses a patient's own immune cells (with or without genetic modification) to treat their cancer. ACT therapies include chimeric antigen receptor (CAR) T cell therapy, T cell receptor (TCR) therapy, and tumor-infiltrating lymphocyte (TIL) therapy. While ACT has proven efficacious in some cancers, objective response rates are generally low in solid tumors. It is thought that success is limited due to heterogeneous antigen expression, loss of cell surface antigen expression during disease progression and immunosuppressive conditions in the tumor microenvironment. TIL therapy is uniquely suited to be insensitive to heterogeneous antigen expression, due to the broad nature of T-cell recognition against both defined and undefined tumors antigens. However, an added challenge is that a significant proportion of TILs have suppressive rather than anti-tumor activity. This was one of the main forces driving development of ACT with genetically modified cells.

To weaken the immunosuppressive conditions within tumors, there has been growing interest in checkpoint inhibitors. Focus has primarily been on the inhibition of cytotoxic T-lymphocyte antigen-4 (CTLA-4) and programmed cell death protein 1 (PD-1), which function as negative regulators of T cell activation, or their ligands B7-1 (CD80) and B7-2 (CD86) and PD-L1 and PD-L2, respectively. Recent clinical trials have demonstrated that immune checkpoint blockade can lead to a prolonged overall survival and an increase in the objective response rate in some types of cancer, including melanoma, non-small cell lung cancer, renal cell carcinoma, and urothelial bladder cancer. However, like ACT, a beneficial effect is only seen in a minority of patients, e.g. 30% in melanoma and 20% in non-small cell lung cancer. Efficacy seems to be correlated with the mutational landscape, where some patients have an insufficient number and/or repertoire of neoantigens to evoke a strong host immune response. Accordingly, higher T cell infiltration has been associated with responsiveness to checkpoint blockade. These findings suggest that tumors that do not respond to immune checkpoint blockade would benefit from immunotherapies that stimulate the T cell response. This has led to the exploration of treatments that combine ACT and checkpoint inhibitors. While initial results have been promising, many of the same limitations faced by ACT as a stand-alone therapeutic are likely to still exist.

In addition to the cell-mediated response to tumor antigens, the humoral response results in autoantibodies that specifically recognize tumors. As used herein, autoantibodies that particularly recognize tumors and bind to the tumors are also called "endogenous antibodies" and "endogenous anti-tumor autoantibodies." The unique specificity of tumor-associated autoantibodies that are found in circulation in the serum have led them to be widely evaluated as biomarkers, prognostic factors, or indicators of tumor recurrence. It has also been shown that there is autoantibody enrichment within malignant tissue. In one study, this was demonstrated in all four of the murine tumor models tested, including three transgenic and one xenograft tumor model. It was found that anti-tumor antibody concentrations were as much a 64-fold higher in tumor tissue compared with normal tissue. This suggests that autoantibodies are particularly well-suited for differentiating between normal and disease pathologies. The potential advantages of using autoantibodies to identify tumor cells (and bind thereto) include (i) their diverse epitope specificity and ability to recognize a broad variety of antigens; (ii) the natural affinity maturation process through which autoantibodies evolve to improve the specificity and strength of binding to tumor antigens; and (iii) the ability of the autoantibody repertoire to continuously adapt to mutations that occur during tumor progression and evolution.

Despite the unique specificity of autoantibodies, the humoral immune response is not sufficient to prevent tumor progression. The present inventors hypothesize that a reason why the humoral response is not able to prevent tumor progression is because autoantibodies lack the therapeutic potency needed to eradicate tumors.

Bispecific antibodies (hereafter "BAb" or "BAbs") have emerged as a highly promising treatment for cancer. BAb physically bring T cells and cancer cells closer together to enhance cancer cell killing. Demonstrating the promise of Bab, Blinatumomab, an anti-CD3×anti-CD19 pair, has produced clinical remission in precursor B cell acute lymphoblastic leukemia at thousand fold lower dosages than rituximab (anti-CD20 monoclonal antibody) and does so without needing a secondary T-cell co-stimulatory signal. Similarly, Catumaxomab (anti-CD3×anti-EpCAM) has led to clinical benefit in patients with malignant ascites with just four intraperitoneal infusions totaling 230 μg over 11 days. In contrast, conventional antibody therapies require cumulative antibody doses ranging from 5-20 g per patient and months to years of therapy. The inventors hypothesize that if autoantibodies were transformed into bispecific T cell-redirecting autoantibodies they would trigger a robust immune response and enhance to potency of checkpoint inhibitors by aiding in the recruitment of more T cells to the tumor tissue.

While many BAb platforms and methods to create BAbs exist, current techniques are not able to transform native autoantibodies into BAbs, with high purity. Chemically-crosslinking an anti-CD3 targeting domain to autoantibodies is one option, but this approach results in aggregates and very low amounts of functional product. Alternatively, mild reducing agents can be used to break inter heavy chain bonds of anti-CD3 antibodies and autoantibodies. Bispecific antibodies can then be formed from antibody mixtures under oxidizing conditions. However, due to random association between antibody light and heavy chains, only ~⅛ of the resulting antibodies will have the desired dual specificity. All other BAb platforms require genetic modifications, and thus cannot be used to transform native autoantibodies into bispecific antibodies.

Embodiments of the present invention harness a patient's antibodies, as opposed to their T cells, to confer specificity for tumor antigens. The immune system generates autoantibodies that can recognize tumors and evolve with disease progression. Anti-tumor antibodies are found within tumors at concentrations that are up to 64-fold higher than normal tissue. This makes autoantibodies well-suited for differentiating between normal and disease pathologies. Embodiments of the present invention exploit this specificity and next generation site-specific bioconjugation technologies to transform endogenous antibodies into highly potent bispecific T cell-redirecting antibodies. Bispecific antibodies have been shown to produce clinical remission in cancer patients at thousands-fold lower dosage than conventional antibody therapies. The inventors hypothesize that the enhanced potency of autoantibodies in a bispecific format will trigger a robust immune response and will enhance the potency of checkpoint inhibitors by aiding in the recruitment of more T cells to the tumor tissue. This represents a paradigm-shifting approach to cancer treatment that is motivated by the inability of current immunotherapies to address the heterogeneity in antigen expression and/or the loss of cell surface antigen expression during disease progression. It is envisioned that the diverse repertoire of endogenous antibodies that will directed against tumor antigens in combination with the ability of autoantibodies to continuously evolve against new tumor antigens will make it difficult for tumors to escape detection.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In this disclosure the singular forms "a," "an," and "the" include the plural reference, and reference to a particular numerical value includes at least that particular value, unless the context clearly indicates otherwise. Thus, for example, a reference to "a compound" refers to one or more of such compounds and equivalents thereof known to one skilled in the art, and so forth. The term "plurality," as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The terms "subject," "individual" and "patient" are used interchangeably herein, and refer to an animal, such as a human, to whom treatment, including prophylactic treatment, with a pharmaceutical composition described herein is provided. The term "subject" as used herein refers to human and non-human animals. The terms "non-human animals" and "non-human mammals" are used interchangeably and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens and turkeys.

In one aspect, this invention provides a bispecific cytotoxic lymphocyte or macrophage-redirecting autoantibody comprising a cytotoxic lymphocyte or macrophage targeting domain and an autoantibody. In an embodiment, the cytotoxic lymphocyte is a T cell or natural killer cell. In an embodiment, the autoantibody is an IgG molecule that is isolated from a patient and is against a tumor, autoantigen, or foreign body, wherein the foreign body is a virus, bacteria, or parasite. In an embodiment, the cytotoxic lymphocyte or macrophage targeting domain is an antibody or an antibody fragment, wherein the antibody is Immunoglobulin G (IgG) and the antibody fragment is an Fc, a single chain Fv (scFv), an Fab, Fab', Fv, F(ab')$_2$, affibody, nanobody, single domain antibody, monobody, anticalin, DARPin, Centyrin, Knottin, variant thereof. In an embodiment, the cytotoxic lymphocyte or macrophage targeting domain is fused to a photoreactive antibody-binding domain (pAbBD), wherein the pAbBD contains a photoreactive crosslinker that is photoreactively conjugated to an autoantibody isolated from a living subject.

In particular embodiments, the pAbBD includes a photoreactive unnatural amino acid and the photoreactive unnatural amino acid is benzyl-phenylalanine. In an embodiment, the antibody-binding domain is created from a thermally stable domain of protein G (HTB1). As used herein, the term "Protein G," refers to a B1 domain based of *Streptococcal* Protein G. Preferably, the Protein G is a hypothermophilic variant of a B1 domain based of *Streptococcal* Protein G.

The amino acid sequence of Protein G preferably is: MTFKLIINGKTLKGEITIEAVDAAEAEKIFKQYANDY-GIDGEWTYDDATKTFTVTE (SEQ ID NO: 1), as described in WO2016/183387, published Nov. 17, 2016, which is incorporated herein by reference in its entirety.

As described in WO2016/183387, nine Protein G variants were successfully designed and expressed, each having an Fc-facing amino acid substituted by BPA: V21, A24, K28, 129, K31, Q32, D40, E42, W42; two variants, A24BPA and K28BPA, allowed ~100% of all human IgG subtypes to be labeled (see FIG. 6 of WO2016/183387). In some embodiments, the Protein G amino acid sequence may include an amino acid sequence with 60, 65, 70, 75, 80, 85, 90, 95 or 99% identity to the sequence set forth in SEQ ID NO: 1. Protein G naturally bind to a broad range of IgGs at the CH2-CH3 junction.

In various embodiments, the T cell targeting domain targets a CD3 receptor.

In an embodiment, the anti-T cell targeting domain is an scFv. In an embodiment, the scFv is an anti-CD3 scFv. In an embodiment, the anti-CD3 scFv is an scFv of anti-human CD3 murine monoclonal antibody OKT-3 having a binding specificity for CD3εγ and CD3εδ. In an embodiment, the scFv has a $(GGS)_2$ linker. In an embodiment, the scFv has a $(GGS)_3$ linker. In an embodiment, the scFv has a $(GGS)_5$ linker.

In an embodiment, the anti-CD3 scFv is an scFv of anti-human CD3 murine monoclonal antibody UCHT1 having a binding specificity for CD3εγ and CD3εδ and has a $(GGS)_3$ linker.

In an embodiment, the anti-CD3 scFv is an scFv of anti-human CD3 murine monoclonal antibody SP34 having a binding specificity for CD3ε, CD3εγ and CD3εδ and has a $(GGS)_3$ linker.

In various embodiments, the natural killer (NK) cell targeting domain targets an NK cell receptor such as CD16, CD16A, IPH61, NKG2D, NKp46, NKp30, or DNAM-1.

In some embodiments, the macrophage targeting domain targets a macrophage receptor such as CD47, CD89 or CD16A.

In some embodiments, the autoantibody is an immunoglobulin G (IgG). In an embodiment, the IgG is a mammalian IgG. In an embodiment, the mammalian IgG is a full-length human IgG. In some embodiments, the bispecific cytotoxic lymphocyte or macrophage-redirecting autoantibody is trivalent or tetravalent.

In another aspect, this invention provides a method for producing a bispecific cytotoxic lymphocyte or macrophage-redirecting autoantibody, comprising: isolating an endogenous autoantibody from sera of a living subject having a tumor or foreign body; covalently conjugating the isolated endogenous autoantibody to a cytotoxic lymphocyte or macrophage targeting domain, wherein the cytotoxic lymphocyte or macrophage targeting domain is fused to a photoreactive antibody-binding domain (pAbBD), and the pAbBD contains a photoreactive crosslinker, that upon irradiating with long wavelength UV light covalently links the pAbBD and the cytotoxic lymphocyte or macrophage targeting domain to the isolated endogenous autoantibody, thereby producing the bispecific cytotoxic lymphocyte or macrophage-redirecting autoantibody.

In some embodiments, the photocrosslinker is a photoreactive unnatural amino acid. In an embodiment, the photoreactive unnatural amino acid is benzyl-phenylalanine. In an embodiment, the antibody-binding domain is derived from a thermally stable domain of protein G (HTB1).

In some embodiments, the T cell receptor is a CD3 receptor. In some embodiments, the scFv is an anti-CD3 scFv. In other embodiments, the anti-CD3 scFv is an scFv of anti-human CD3 murine monoclonal antibody OKT-3 having a binding specificity for CD3εγ and CD3εδ. In an embodiment, the scFv has a $(GGS)_2$ linker. In another embodiment, the scFv has a $(GGS)_3$ linker. In a further embodiment, the scFv has a $(GGS)_5$ linker. In another embodiment, the anti-CD3 scFv is an scFv of anti-human CD3 murine monoclonal antibody UCHT1 having a binding specificity for CD3εγ and CD3εδ and has a $(GGS)_3$ linker. In other embodiments, the anti-CD3 scFv is an scFv of anti-human CD3 murine monoclonal antibody SP34 having a binding specificity for CD3ε, CD3εγ and CD3εδ and has a $(GGS)_3$ linker.

In some embodiments, the autoantibody is an immunoglobulin G (IgG). In an embodiment, the IgG is a mammalian IgG. In another embodiment, the mammalian IgG is a full-length human IgG. In particular embodiments, the isolated bispecific TRAAb is tetravalent.

In another aspect, provided herein are methods of treating a subject in need thereof by administering to the subject an isolated bispecific cytotoxic lymphocyte or macrophage-redirecting autoantibody comprising a cytotoxic lymphocyte or macrophage targeting domain photoreactively conjugated to an autoantibody of a living subject, where the antibody-binding domain comprises a photoreactive crosslinker. In some embodiments, the subject has cancer, e.g., breast cancer. In other embodiments, the subject has a viral, bacterial or parasite infection.

In some embodiments, the photoreactive unnatural amino acid is benzyl-phenylalanine. In various embodiments, the antibody-binding domain is derived from a thermally stable domain of protein G (HTB1). In an embodiment, the T cell receptor is a CD3 receptor.

In some embodiments, the scFv is an anti-CD3 scFv. In an embodiment, the anti-CD3 scFv is an scFv of anti-human CD3 murine monoclonal antibody OKT-3 having a binding specificity for CD3εγ and CD3εδ. In an embodiment, the scFv has a $(GGS)_2$ linker. In an embodiment, the scFv has a $(GGS)_3$ linker. In an embodiment, the scFv has a $(GGS)_5$ linker. In an embodiment, the anti-CD3 scFv is an scFv of anti-human CD3 murine monoclonal antibody UCHT1 having a binding specificity for CD3εγ and CD3εδ and has a $(GGS)_3$ linker. In an embodiment, the anti-CD3 scFv is an scFv of anti-human CD3 murine monoclonal antibody SP34 having a binding specificity for CD3ε, CD3εγ and CD3εδ and has a $(GGS)_3$ linker. In an embodiment, the autoantibody is an immunoglobulin G (IgG). In an embodiment, the IgG is a mammalian IgG. In an embodiment, the mammalian IgG is a full-length human IgG. In some embodiments, the bispecific T-cell-redirecting autoantibody is trivalent or tetravalent. In an embodiment, the subject has breast cancer. In another embodiment, the methods for treating cancer further comprise administering to the subject an anti-Programmed Cell death protein ligand 1 (PDL1) antibody.

All patents and literature references cited in the present specification are hereby incorporated by reference in their entirety.

EXAMPLES

The Examples below show that a living subject's endogenous antibodies, including endogenous anti-tumor antibodies, can be transformed into bispecific T cell-redirecting autoantibodies (TRAAbs) and enhance the immune system's ability to specifically suppress and/or eradicate malignant cells. This represents a paradigm-shifting approach to cancer treatment that is motivated by the inability of current immunotherapies to address heterogeneity in antigen expression and/or loss of cell surface antigen expression during tumor progression. The diverse epitope specificity and ability of the autoantibody repertoire to continuously evolve with tumor progression, make them uniquely suited for this task. Moreover, the potent cytolytic potential of bispecific antibodies make them a preferred platform for antibody-based therapeutics. In addition to testing TRAAbs as a stand-alone therapy, whether TRAAbs can aid in recruiting T cells into tumor tissue to enhance the potency of immune checkpoint inhibitor therapy is also tested.

Example 1: One-Step Production of TRAAbs

TRAAbs are generated using a novel, one-step bioconjugation strategy that allows site-specific and covalent attachment of an anti-CD3 single chain variable fragment (scFv) to native human Immunoglobulin G (IgG) (FIG. 1). The TRAAbs production technique relies on a small antibody-binding domain that is engineered to contain a photoreactive unnatural amino acid (benzoyl-phenylalanine, BPA) in its Fc-binding site. The photoreactive antibody-binding domain (pAbBD) is created from a small (~6.5 kD), thermally stable domain of Protein G (HTB1), as described in Meyer S C, Huerta C, Ghosh I. Single-site mutations in a hyperthermophilic variant of the B1 domain of Protein G result in self-assembled oligomers. Biochemistry. 2005; 44(7):2360-8, and WO2016/183387, each of which is incorporated herein by reference in its entirety.

In WO2016/183387, of the nine Protein G variants successfully designed and expressed, two variants, A24BPA and K28BPA, allowed ~100% of all human IgG subtypes to be labeled as shown in FIG. 6 therein.

Figures 2A, 2B:
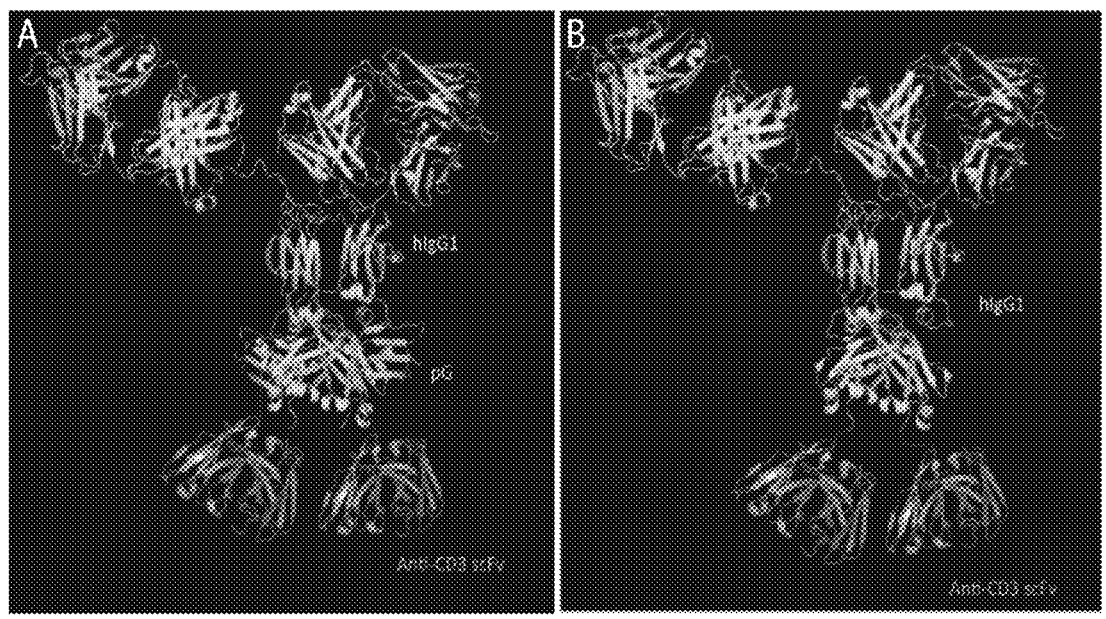
FIGS. 2A-2B. Predicted chemical structure of BAb formed through (2A) the photo-crosslinking of pAbBD-scFv to IgG1 and (2B) genetic fusion of scFvs to the C-termini of IgG1. The structure of the BAb in (A) was created by aligning the structure of the whole human IgG1(1HZH.pdb) and IgG1 Fc-Protein G monomer (pG) complex (1FCC.pdb). The anti-CD3 scFv (1XIW.pdb) structure was positioned manually. Both images were created using PyMOL software.

Introduction of a photoreactive amino acid allows for the formation of a covalent linkage between a pAbBD-scFv fusion protein and IgG, to prevent dissociation in serum. The pAbBD is able to binding to both heavy chains of IgG, thereby creating a tetravalent BAb that is structurally similar to genetically engineered BAbs (FIG. 2) that are in clinical trials (e.g., Sanofi/SARI 56597, Merrimack/MM141, and Aptevo/Mor209/ES414, each of which is incorporated herein by reference in its entirety). Binding of Protein G to Fc sites of IgG does not prevent or sterically interfere with the attachment of these antibodies to the Fc receptor, as described by Cai Z, Fu T, Nagai Y, Lam L, Yee M, Zhu Z, Zhang H. scFv-based "Grababody" as a general strategy to improve recruitment of immune effector cells to antibody-targeted tumors. Cancer Res. 2013; 73(8):2619-27, and Sulica A, Medesan C, Laky M, Onica D, Sjoquist J, Ghetie V. Effect of protein A of *Staphylococcus aureus* on the binding of monomeric and polymeric IgG to Fc receptor-bearing cells. Immunology. 1979; 38(1):173-9, each of which is incorporated herein by reference in its entirety. Therefore, TRAAbs are expected to retain ADCC and CDC function. Protein G does interfere with FcRn binding, as described by Derrick J P, Wigley D B. Crystal structure of a streptococcal protein G domain bound to an Fab fragment. Nature. 1992; 359(6397):752-4 and Roopenian D C, Akilesh S. FcRn: the neonatal Fc receptor comes of age. Nat Rev Immunol. 2007; 7(9):715-25, each of which is incorporated herein by reference in its entirety. Therefore, a shortened circulation time is expected compared with native IgG. TRAAbs will be evaluated for their properties, including ADCC and CDC function and circulation time.

Example 2: Preparation of BAbs Using pAbBD-scFv Fusion Proteins, Functionality Chemically-Crosslinked BAbs and TRAAb Therapy in Mouse Model of Breast Cancer In Vivo Incorporation of BPA into Protein G HTB1 During Protein Expression:

To incorporate the unnatural amino acid benzoylphenyl-alanine (BPA) into the Protein G HTB1 sub-domain during translation, site-directed mutagenesis was used to introduce an amber codon into the IgG binding site of Protein G HTB1. Host *E. coli* were co-transformed with the plasmids encoding for photoreactive protein G or wild-type protein G and the pEVOL-pBpF plasmid (Addgene), which carries the tRNA/aminoacyl transferase pair, as described by Young T S, et al., An enhanced system for unnatural amino acid mutagenesis in *E. coli*. J Mol Biol. 2010; 395(2):361-74, which is incorporated herein by reference in its entirety. While wild-type Protein G HTB1 was expressed in the absence of BPA, the mutant containing the amber codon required BPA for expression. There was no detectable "leaky" background incorporation of other amino acids in response to the amber codon and the expression level for the BPA-containing mutant protein was comparable to that of the wild type Protein G HTB1, as described by Hui J Z, Al Zaki A, Cheng Z, Popik V, Zhang H, Luning Prak E T, Tsourkas A. Facile method for the site-specific, covalent attachment of full-length IgG onto nanoparticles. Small. 2014; 10(16):3354-63, which is incorporated herein by reference in its entirety.

Figure 3:
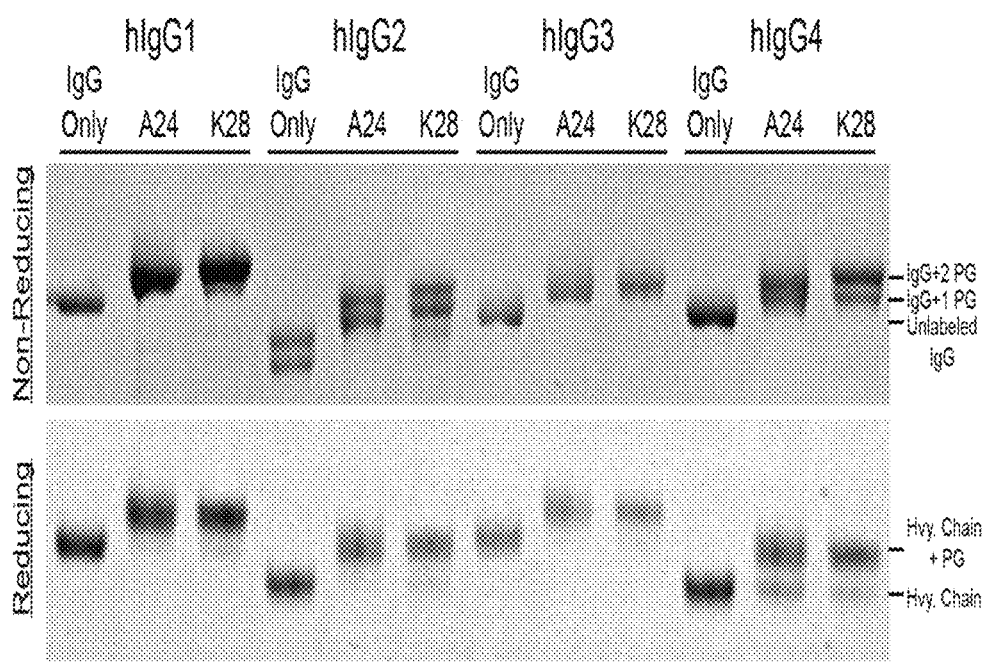
FIG. 3. Non-reducing (upper panel) and reducing (lower panel) SDS-PAGE gels of various human IgG subclasses alone or after photocrosslinking with Protein G-based adapter proteins. The adapter proteins possessed either a A24BPA or K28BPA substitution (BPA=benzoylphenylalanine). Conjugation was done for one hour and 30 minutes using four equivalents of Protein G. Note hIgG2 isotype used here naturally presents as two bands on non-reducing gel.

Protein G-IgG Crosslinking:

To optimize crosslinking of the pAbBDs with human IgG, nine Protein G HTB1 variants were designed and expressed, each with an Fc-facing amino acid substituted by BPA. Expression yields for all variants were high at around 5 mg/mL, consistent with reports of BPA incorporation into proteins as described by Chin J W, Martin A B, King D S, Wang L, Schultz P G. Addition of a photocrosslinking amino acid to the genetic code of Escherichiacoli. Proc Natl Acad Sci USA. 2002; 99(17): 11020-4, which is incorporated herein by reference in its entirety. Next, these variants were screened for their ability to covalently label all human IgG subclasses upon exposure to long wavelength UV light (FIG. 3). Since each IgG is composed of two identical heavy chains, it can be labeled with up to two pAbBDs, which can be deciphered using non-reducing SDS-PAGE. Two Protein G variants, A24BPA ($PG^{A24}$) and K28BPA ($PG^{K28}$), were found that allowed ~100% of all human IgG subclasses to be labeled with at least one adapter protein. More than 90% of all human IgG subclasses were labeled with two pAbBDs (i.e. one pAbBD per heavy chain). In addition, the inventors have identified pAbBDs that are capable of efficiently cross-linking all mouse (mIgG1, 2a,2b,2c,3) as well as some rat, rabbit, hamster, and goat IgG, as described in Hui J Z, et al., Small. 2014; 10(16):3354-63 and Hui J Z, Tsourkas A. Optimization of photoactive protein Z for fast and efficient site-specific conjugation of native IgG. Bioconjug Chem. 2014; 25(9):1709-19, each of which is incorporated herein by reference in its entirety.

Figures 4A, 4B:
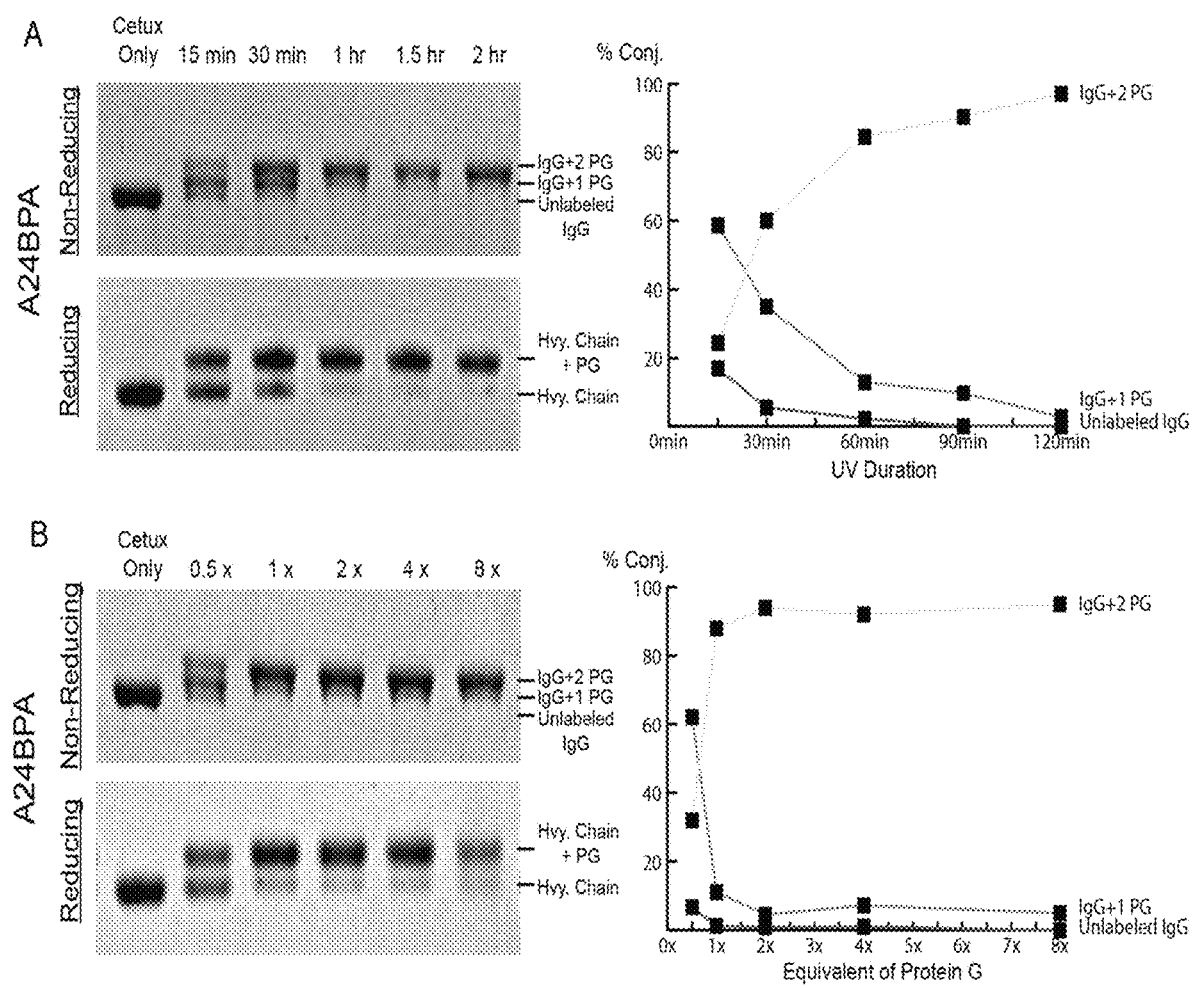
FIGS. 4A-4B. Non-reducing and reducing SDS-PAGE of cetuximab (Cetux, human IgG1) alone or after photocrosslinking with $PG^{A24}$ for (FIG. 4A) varying periods of time using four equivalents of adapter protein or (FIG. 4B) with various molar ratios of adapter protein-to-IgG UV crosslinking was performed for one hour and 30 minutes. Image analysis of non-reducing gels are shown on the right.

Kinetics and Efficiency of pAbBD-IgG Crosslinking:

pAbBDs covalently crosslink IgG with extremely fast kinetics. After only 30 minutes of exposure to long wavelength UV light, 95% of IgG was conjugated with one or two pAbBDs (FIG. 4A). The reaction is nearly stoichiometric with complete conjugation of IgG using just one equivalent of AbBD (FIG. 4B). Similar conjugation efficiencies are reproducible for different IgGs of the same subclass. Similar results are also achievable using other readily available UV light sources and in a variety of common buffers.

Stability and Inertness of the Adapter Protein, pAbBDs:

The pAbBD includes BPA, which is only activated by non-harmful long wavelength UV light (365 nm) and is only quenched if in close proximity to a target (10 Å) with which it can form a covalent bond. Therefore, pAbBDs are safe to use, stable under ambient light, and non-reactive towards other proteins that it cannot bind, as described by Dorman G, Prestwich G D. Benzophenone photophores in biochemistry. Biochemistry. 1994; 33(19):5661-73, which is incorporated herein by reference in its entirety. Moreover, antigen binding affinity is preserved after UV crosslinking of an IgG with a pAbBD, as described by Hui J Z, Tamsen S, Song Y, Tsourkas A. LASIC: Light Activated Site-Specific Conjugation of Native IgGs. Bioconjug Chem. 2015; 26(8):1456-60, which is incorporated herein by reference in its entirety. The exquisite specificity of the pAbBD towards IgG allows for efficient conjugation even in the presence of other proteins, which may be present in some IgG samples, as described by Hui J Z, et al., Small. 2014; 10(16):3354-63, which is incorporated herein by reference in its entirety. This was shown by labeling hIgG2, either by itself or in 1% BSA solution (200-times molar excess). A similarly high level of hIgG2 was labeled by Protein G in the presence and absence of BSA. No BSA labeling was detected.

Figure 5:
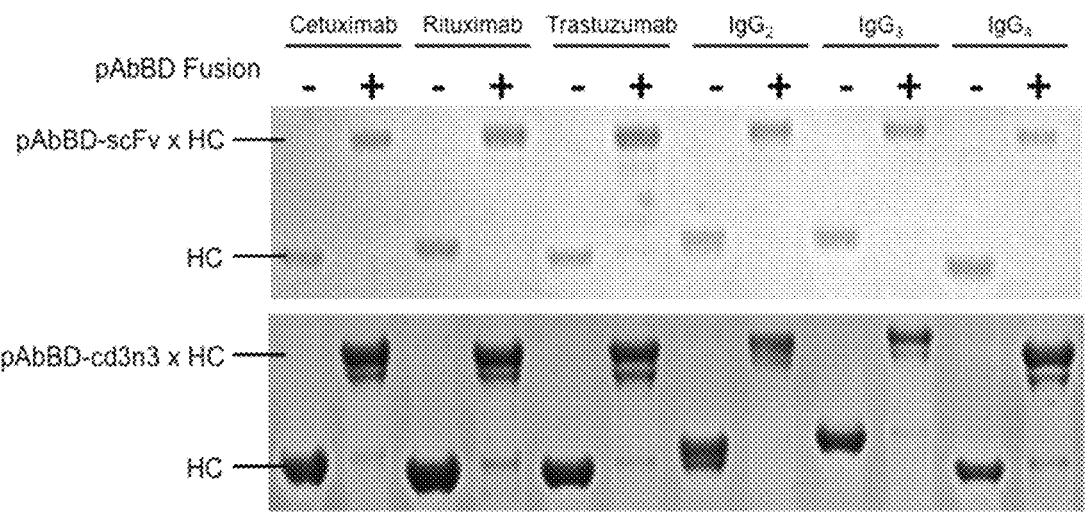
FIG. 5. Reducing SDS-PAGE of six different human antibodies—Rituximab, Cetuximab, Trastuzumab, IgG2, IgG3, and IgG4—alone or after photo-crosslinking with (FIG. 5, top) a pAbBD-anti-CD3 scFv or (FIG. 5, bottom) pAbBD-anti-CD3 nanobody. Free pAbBD-scFv or pAbBD-nanobody was efficiently removed via filtration. The bands represent IgG heavy chains (HC) before and after photo-crosslinking.

Formation of BAbs Using pAbBD-scFv Fusion Proteins:

To prepare BAbs, a pAbBD was fused to an anti-CD3 scFv (OKT3 parent antibody). The expressed pAbBD-scFv was then simply mixed with the IgG of choice and photocrosslinked for 2 hrs. To demonstrate the simplicity of the approach, six unique BAb were simultaneously created in parallel (FIG. 5, top gel). Because of the high crosslinking efficiency between the pAbBD and IgG, essentially just two species exist after the photoreaction, diconjugated IgG, i.e. two pAbBD per IgG (one pAbBD per heavy chain) and free pAbBD-scFv. This makes it extremely easy to obtain highly pure tetravalent BAb, since the free pAbBD is easily removed using ultrafiltration spin columns (100 kDa MWCO, Millipore) or diafiltration, if large volumes are used. If necessary, mono-conjugated IgG and unconjugated IgG can be removed using Protein A/G beads, since the pAbBD sterically blocks the di-conjugated IgG from interacting with Protein A/G.

BAbs were also prepared by fusing a pAbBD to an anti-CD3 nanobody (CD3n3). As before, the expressed pAbBD-CD3n3 was then simply mixed with the IgG of choice and photocrosslinked for 2 hrs. Six unique BAb were simultaneously created in parallel (FIG. 5, bottom gel).

Figures 6A, 6B:
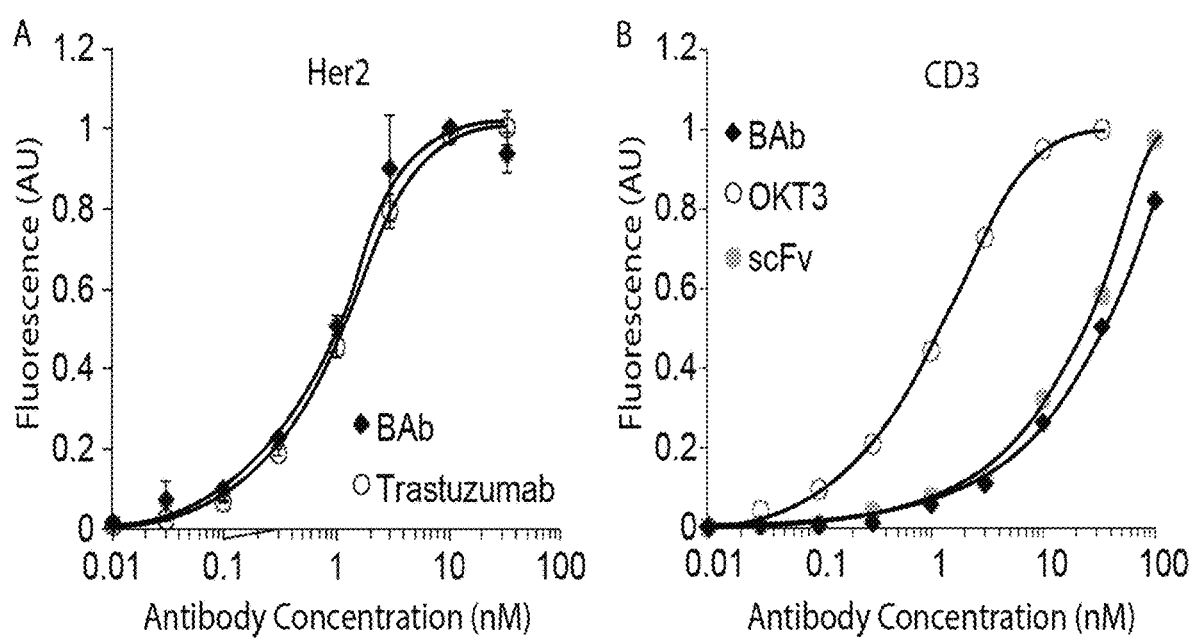
FIGS. 6A-6C. Binding studies of chemically-crosslinked unconjugated antibodies.

BAb Affinity Vs. Analogous Monoclonal Antibodies:

To demonstrate that photocrosslinking of pAbBD-scFvs to IgG has no effect on antibody binding, the affinity of chemically-crosslinked anti-Her2 (Trastuzumab)×anti-CD3, anti-EGFR (Cetuximab)×anti-CD3, and anti-CD20 (rituximab)×anti-CD3 BAb were compared to their respective unconjugated, mono-specific human antibodies from which they were derived (FIGS. 6A-6B). The bispecific and monospecific antibodies were incubated with the respective Her2-, EGFR, or CD20-positive cancer cells and the level of binding was quantified using fluorescently-labeled secondary antibodies. Analysis of the fluorescent signals indicated that there was no significant difference in binding affinity between the BAb and the corresponding unconjugated, monospecific antibodies, confirming that the site-specific chemical attachment of an scFv to IgG does not interfere with antigen binding.

The binding of chemically-crosslinked BAbs to CD3-positive T cells was compared to full-length anti-CD3 antibody (OKT3) and single anti-CD3 scFvs. Interestingly, the BAb exhibited an affinity similar to a single scFv, despite having two anti-CD3 binding domains. Similar findings were reported for genetically engineered BAbs, with an anti-CD3 scFv fused to the C-terminus of each heavy chain, as described by Lu C Y, Chen G J, Tai P H, Yang Y C, Hsu Y S, Chang M, Hsu C L. Tetravalent anti-CD20/CD3 bispecific antibody for the treatment of B cell lymphoma. Biochem Biophys Res Commun. 2016; 473(4):808-13, which is incorporated herein by reference in its entirety. It was speculated that this is because the two anti-CD3 scFvs are physically not able to simultaneously bind to two CD3 receptors, which alleviates concerns over CD3 crosslinking and a cytokine storm, as described by Chatenoud L, Bluestone J A. CD3-specific antibodies: a portal to the treatment of autoimmunity. Nat Rev Immunol. 2007; 7(8):622-32; Gall J M, Davol P A, Grabert R C, Deaver M, Lum L G. T cells armed with anti-CD3×anti-CD20 bispecific antibody enhance killing of CD20+ malignant B cells and bypass complement-mediated rituximab resistance in vitro. Exp Hematol. 2005; 33(4):452-9; Moore G L, Bautista C, Pong E, Nguyen D H, Jacinto J, Eivazi A, Muchhal U S, Karki S, Chu S Y, Lazar G A. A novel bispecific antibody format enables simultaneous bivalent and monovalent co-engagement of distinct target antigens. MAbs. 2011; 3(6):546-57; Perruche S, Zhang P, Maruyama T, Bluestone J A, Saas P, Chen W. Lethal effect of CD3-specific antibody in mice deficient in TGF-beta1 by uncontrolled flu-like syndrome. J Immunol. 2009; 183(2):953-61; and Stebbings R, Poole S, Thorpe R. Safety of biologics, lessons learnt from TGN1412. Curr Opin Biotechnol. 2009; 20(6):673-7, each of which is incorporated herein by reference in its entirety. As a result, several clinical studies have already been initiated with BAbs that are bivalent for CD3 (ClinicalTrials.gov Identifier: NCT02106091, NCT02262910, each of which is incorporated herein by reference in its entirety).

Figure 6C:
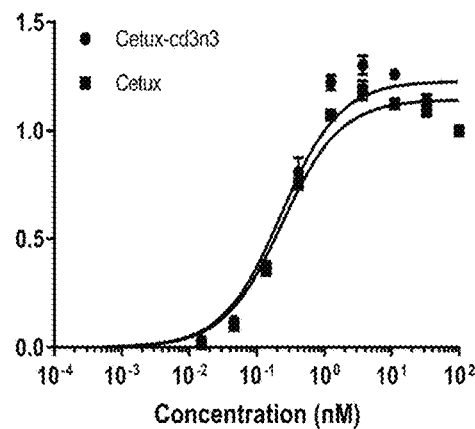

It was also demonstrated that photocrosslinking of pAbBD-CD3n3 (nanobody) to IgG had no effect on antibody binding, the affinity of chemically-crosslinked anti-EGFR (Cetuximab)×anti-CD3 was compared to Cetuximab alone (FIG. 6C). The bispecific and monospecific antibodies were incubated with EGFR-positive cancer cells and the level of binding was quantified using fluorescently-labeled secondary antibodies. Analysis of the fluorescent signals indicated that there was no significant difference in binding affinity between the BAb and the corresponding unconjugated, monospecific antibodies, confirming that the site-specific chemical attachment of a nanobody to IgG does not interfere with antigen binding.

Figures 7A, 7B, 7C:
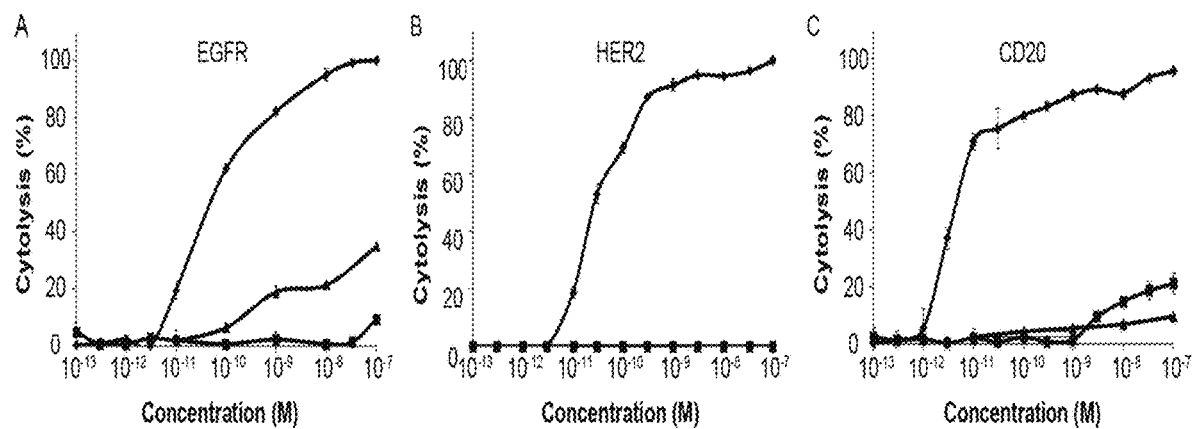
FIGS. 7A-7C. T cell-mediated cytolysis of (FIG. 7A) EGFR-positive, (FIG. 7B) Her2-positive, or (FIG. 7C) CD20-positive target cancer cells as a function of antibody dose, 12 hrs after the administration of different concentrations of anti-EGFR, anti-Her2, and anti-CD20×anti-CD3 BAb (black diamond), respectively; a mixture of the respective unconjugated antibodies and anti-CD3 scFvs (black squares); or a non-targeted IgG×anti-CD3 bispecific antibody (black triangle). All assays were performed with enriched T cells at a 10:1 effector-to-target ratio.

Functionality of Chemically-Crosslinked BAbs:

To demonstrate that the chemically-crosslinked BAbs provide a potent therapeutic effect, T cell-mediated cell lysis assays were performed. Specifically, chemically-crosslinked anti-Her2 (Trastuzumab)×anti-CD3, anti-EGFR (Cetuximab) anti-CD3, and anti-CD20 (rituximab)×anti-CD3 BAb were incubated with the respective Her2-, EGFR-, or CD20-positive cancer cells. T cells were added at a 10:1 effector-to-target ratio and cell lysis was monitored using an xCELLigence real-time cell analysis (RTCA) instrument for 48 hours. All the BAbs exhibited a dose-dependent cytotoxic effect with an $EC_{50}$ in the 1-50 pM range, 12 hrs post-treatment (FIGS. 7A-7C). The potency of the chemically-crosslinked BAbs appear to be similar or better than what others have observed with other BAb formats, as described by Gall J M, Davol P A, Grabert R C, Deaver M, Lum L G. T cells armed with anti-CD3×anti-CD20 bispecific antibody enhance killing of CD20+ malignant B cells and bypass complement-mediated rituximab resistance in vitro. Exp Hematol. 2005; 33(4):452-9; Stanglmaier M, Faltin M, Ruf P, Bodenhausen A, Schroder P, Lindhofer H. Bi20 (fBTA05), a novel trifunctional bispecific antibody (anti-CD20×anti-CD3), mediates efficient killing of B-cell lymphoma cells even with very low CD20 expression levels. Int J Cancer.

2008; 123(5):1181-9; and Sun et al., Anti-CD20/CD3 T cell-dependent bispecific antibody for the treatment of B cell malignancies. Sci Transl Med. 2015; 7(287):287ra70, each of which is incorporated herein by reference in its entirety. Notably, little to no cytotoxicity was observed when a mixture of the unconjugated, monoclonal antibody and the anti-CD3 scFv or non-targeted BAbs were incubated with target cells in the presence of T cells at a 10:1 effector-to-target ratio.

Figures 10A, 10B, 10C:
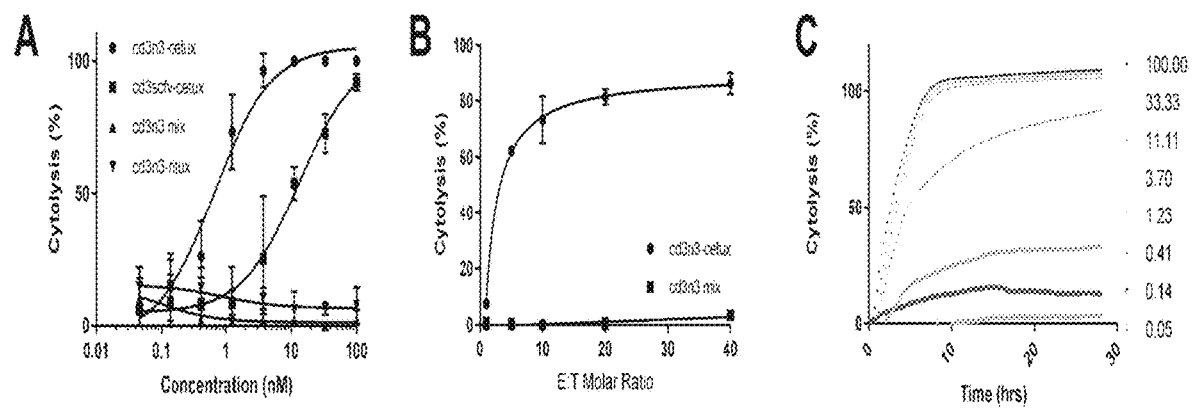
FIGS. 10A-10C. T cell-mediated cytolysis studies with bispecific antibodies prepared by photocrosslinking Cetuximab to pAbBD-anti-CD3 scFv or pAbBD-anti-CD3 nanobody.

Preliminary T cell-mediated cytolysis studies have also been performed using bispecific antibodies prepared by photocrosslinking Cetuximab to a pAbBD-anti-CD3 nanobody. These bispecific antibodies also led to T cell-mediated cytolysis of EGFR-positive MDA-468-MB tumor cells (FIG. 10A) and the potency seemed to be better than bispecific antibodies produced with pAbBD-anti-CD3 scFv fusion proteins. No dose-dependent cytolysis was observed when Cetuximab was mixed with free anti-CD3 nanobody or when cells were incubated with Rituximab (anti-CD20) conjugated with anti-CD3 nanobody. All assays were performed with enriched T cells at a 10:1 effector-to-target ratio. FIG. 10B shows increased cytolysis with Cetuximab× anti-CD3n3 bispecific antibodies as the effector-to-target ratio was increased. In these studies, cytolysis was measured 12 hrs post-treatment with 1 nM bispecific antibody. FIG. 10C shows cytolysis kinetics of Cetuximab photocrosslinked with anti-CD3 nanobody using 10:1 effector-to-target ratio.

Figure 8:
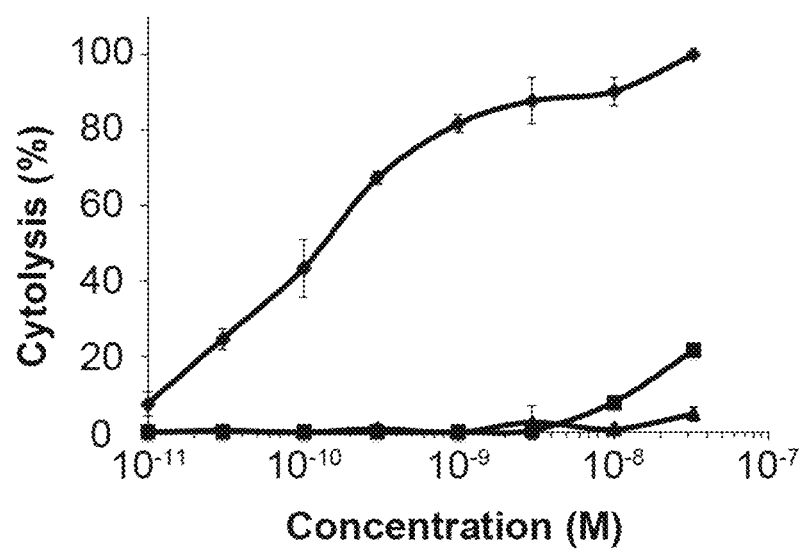
FIG. 8. T cell-mediated cytolysis of EGFR-overexpressing MDA-MB-436 cells as a function of T cell-redirecting autoantibody dose (TRAAbs) (black diamond). TRAAbs were produced by photocrosslinking pAbBD-anti-CD3 scFvs to anti-tumor autoantibodies isolated from immune-competent mice immunized with MDA-MB-436 cells. Analogous studies were performed with a mixture of unconjugated autoantibodies and anti-CD3 scFvs (black squares), or TRAAbs prepared from autoantibodies isolated from wild-type mice (black triangle). All assays were performed with enriched T cells at a 10:1 effector-to-target ratio and cytolysis data was quantified 12 hrs post-administration of TRAAbs.
Figure 11:
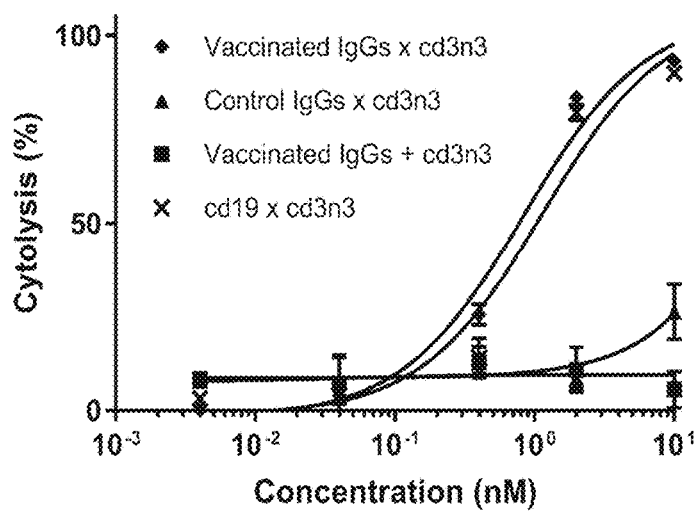
FIG. 11. T cell-mediated cytolysis of Nalm-6 B cell leukemia 24 hrs post-treatment with bispecifics prepared by photocrosslinking pAbBD-anti-CD3 nanobody to IgGs extracted from C57BL/6 mice vaccinated with Nalm6 cells, IgGs extracted from wild-type C57BL/6 mice or anti-CD19 IgGs.

T Cell Re-Directing Autoantibodies:

To provide initial evidence that TRAAb therapy is feasible for the treatment of cancer, C57BL/6 J mice were vaccinated with EGFR-overexpressing MDA-MB-468 breast cancer cells or NALM-6 leukemia cells. Subsequently, mouse blood was collected by cardiac puncture and autoantibodies in the serum were purified using Protein G beads. The purified IgG was photocrosslinked with pAbBD-scFv and purified by spin filtration. The cytolytic potential of the resulting TRAAbs was evaluated in a T cell-mediated cell lysis assay. Specifically, the TRAAbs were incubated with MDA-MB-468 or NALM-6 cancers cells in the presence of T cells at an effector-to-target ratio of 10:1 or 5:1, respectively, and cell lysis was monitored for up to 48 hours. The TRAAbs exhibited a highly potent, dose-dependent cytotoxic effect with an $EC_{50}$ of ~150 pM for MDA-MB-468 (FIG. 8) and ~1.5 nM for NALM-6 cells (FIG. 11), 12 hrs post-treatment. For comparison, bispecific antibodies formed from cetuximab and pAbBD-scFv had an $EC_{50}$ of ~50 pM against MDA-MB-231 (FIG. 7A). Bispecific antibodies formed from anti-CD19 and pAbBD-scFv had the same $EC_{50}$ as TRAAbs against NALM-6 cells (FIG. 11). From this data, it can be loosely inferred that TRAABs have a therapeutic effect that is similar to monoclonal bispecific antibodies (within a factor of 3).

Figure 12:
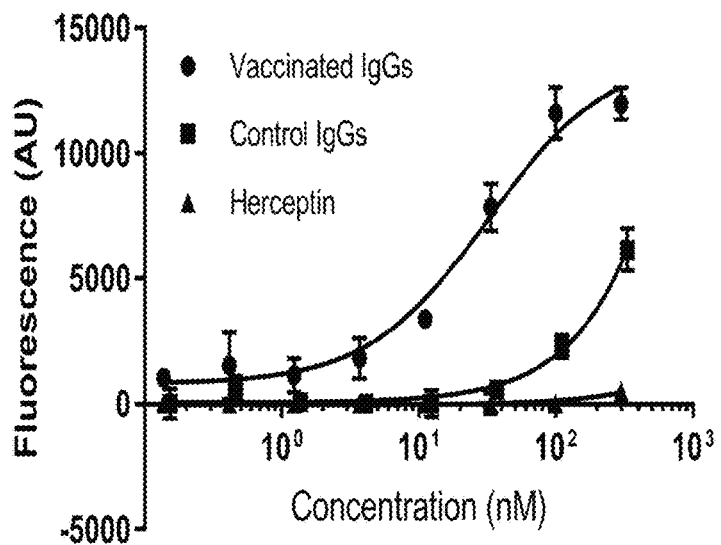
FIG. 12. Dose-dependent binding of anti-tumor IgG autoantibodies isolated from BALB/c mice bearing triple negative breast cancer 4T1 tumors, 0.8-1 cm in diameter (Vaccinated IgGs). Dose-dependent binding was also evaluated for IgG isolated from wild-type BALB/c mice (control IgGs) and Her2-targeted Herceptin.
Figure 13:
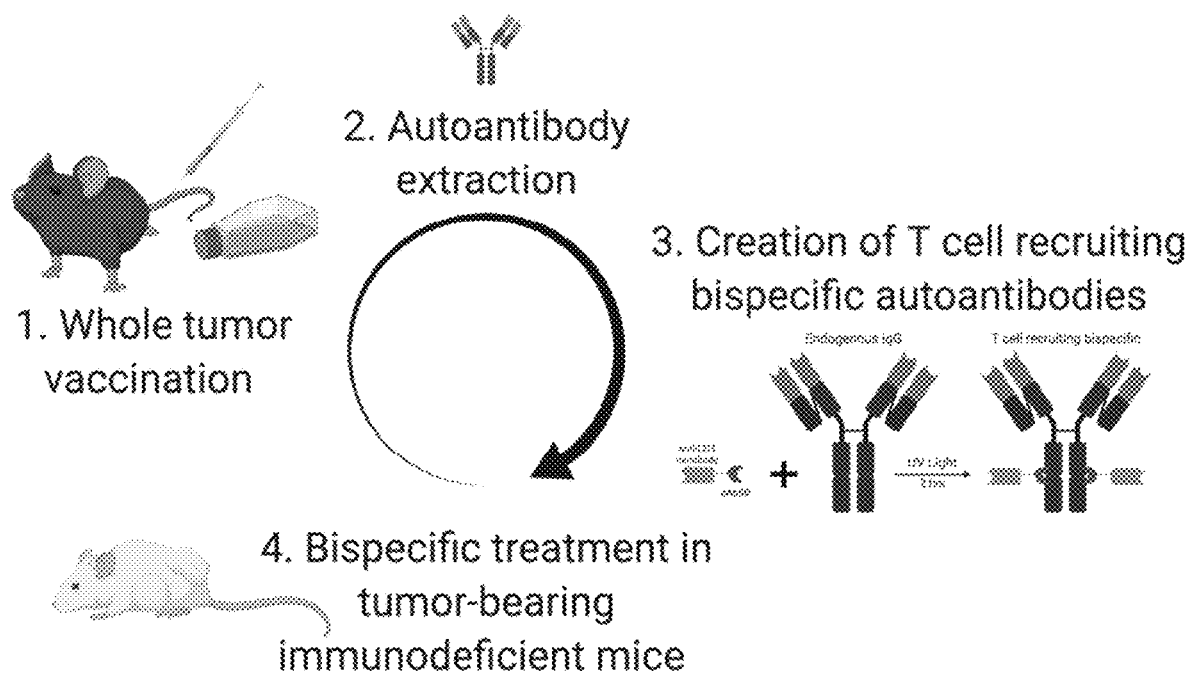
FIG. 13. Autoantibodies are extracted from tumor-bearing mice and converted into T cell recruiting bispecifics via photoreactive, site-specific covalent crosslinking mediated by a photoreactive antibody-binding domain (pAbBD). pAbBD has been designed based off a small domain within the naturally occurring bacterial Protein G. Its native function is to bind IgGs at the CH2-CH3 junction within the heavy chain Fc region. It has been optimized to exclude Fab binding and modified with an amber stop codon to include an unnatural amino that enables covalent crosslinking. pAbBD is expressed in fusion with an anti-CD3 nanobody. In the presence of autoantibody, pAbBD binds each heavy chain. UV exposure drives covalent crosslinking via the unnatural amino acid benzoylphenylalanine (BPA). The tumor killing capability of the resulting bispecific autoantibodies is evaluated in vitro and in vivo using immunodeficient tumor-bearing mice engrafted with human T cells.
Figure 14:
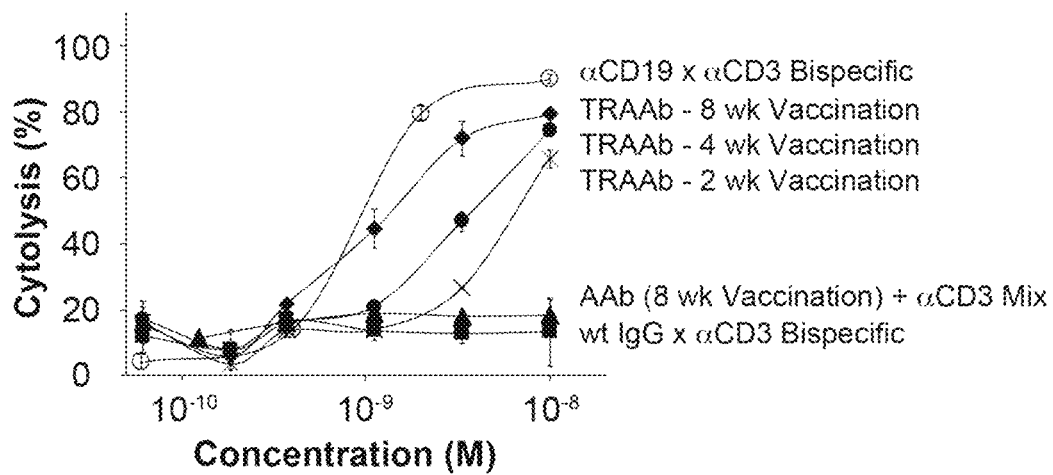
FIG. 14. T cell-mediated cytolysis of Nalm-6 B cell leukemia using 5:1 E:T 24 hrs post-treatment with bispecifics made with anti-CD3 nanobody crosslinked to (i) autoantibodies extracted from C57BL/6 mice that were vaccinated with Nalm-6 cells, (ii) IgGs extracted from wild-type C57BL/6 mice and (iii) anti-CD19 IgGs. Mixture control does not contain pAbBD. Whole tumor vaccination of C57BL/6 immunocompetent mice with Nalm-6 B cell leukemia was completed as follows: two weeks of biweekly i.p. injections with $2\times10^6$ cells are followed by two weeks off. This 28-day cycle is repeated twice before collecting the entire blood volume. Autoantibodies were also collected from samples after the second and fourth weeks. Cells are separated from the serum by high-speed centrifugation, and the antibodies are captured using recombinant Protein G agarose resin.
Figure 15:
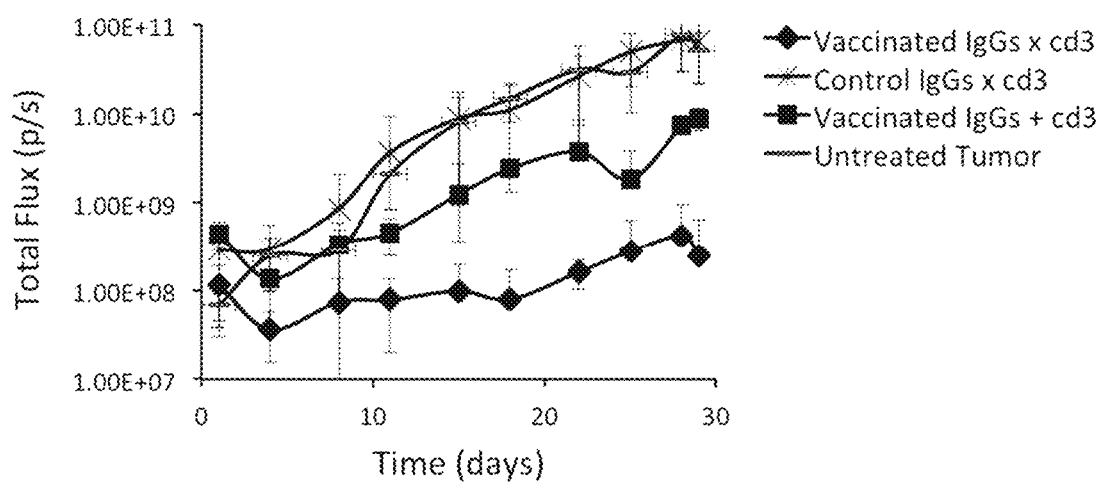
FIG. 15. In vivo tumor delay of Nalm-6 leukemia model in immunodeficient NSG mice dosing at 0.5 mg/kg and using 20:1 E:T. 10M human T cells and 0.5M Nalm-6 cells are administered on day 1, along with a third of the dose corresponding to 0.5 mg/kg. Two additional bispecific treatment doses are administered on days 3 and 5. Each mouse receives 1 mg wild-type polyclonocal murine IgG evenly distributed among the three injection days (BioXCell BE0093). Tumor growth is tracked twice per week via luciferase expression and D-luciferin injections using the IVIS Ilumina system. T cells are obtained from donors through the Penn Human Immunology Core (HIC), expanded and activated using CD3/CD28 Dynabeads, and stored frozen. They are thawed at 1 M/mL in RPMI media 16 hrs before injection. Endotoxins are removed using 1% triton X-114 phase separation. All constructs are dialyzed using 100 kDa as the cut-off in sterile PBS.

In another study, anti-tumor autoantibodics were isolated from Balb/c mice bearing a n orthotopic, triple negative breast cancer 4T1 tumor (0.8-1.0 cm diameter). The purified IgG was photocrosslinked with pAbBD-anti-CD3n3 nanobody. Dose-dependent binding of the TRAAbs (Vaccinated IgG) were then evaluated with 4T1 cells in culture (FIG. 12). It was found that the TRAAbs had an apparent affinity of ~100 nM. Dose-dependent binding was also evaluated for IgG isolated from wild-type BALB/c mice (control IgGs) and Her2-targeted Herceptin. Both of these samples exhibited significantly less binding than the TRAAbs.

Overcoming Potential Immunogenicity of Protein G HTB1:

Since Protein G is derived from *Streptococcal* Protein G, the immunogenicity of TRAAbs, which include subunits of Protein G is a concern. While data on the immunogenicity of Protein G (HTB1 domain) is scarce, there are some preliminary reports that indicate that the immunogenicity of other bacterially derived antibody-binding domains, i.e., Protein A, is minimal, as described by Dima S, et al., Effect of protein A and its fragment B on the catabolic and Fc receptor sites of IgG. Eur J Immunol. 1983; 13(8):605-14; and Fiandra L, et al., Assessing the in vivo targeting efficiency of multifunctional nanoconstructs bearing antibody-derived ligands. ACS Nano. 2013; 7(7):6092-102, each of which is incorporated herein by reference in its entirety. Specifically, Affibodies®, which are based on a Protein A scaffold, have been reported to induce little to no detectable activation of the immune system, as described by Affibody Annual Report, 2003. Available from the Affibody® website; and Sorensen J, et al., First-in-human molecular imaging of HER2 expression in breast cancer metastases using the 111In-ABY-025 affibody molecule. J Nucl Med. 2014; 55(5):730-5, each of which is incorporated herein by reference in its entirety.

Notably, if the pAbBD-scFv is found to be immunogenic, there are many approaches that have been developed to reduce the immunogenicity of recombinant proteins, as described by De Groot A S, Moise L. Prediction of immunogenicity for therapeutic proteins: state of the art. Curr Opin Drug Discov Devel. 2007; 10(3):332-40; Jawa V, et al., T-cell dependent immunogenicity of protein therapeutics: Preclinical assessment and mitigation. Clin Immunol. 2013; 149(3):534-55; and Salazar-Fontana L I, et al., Approaches to Mitigate the Unwanted Immunogenicity of Therapeutic Proteins during Drug Development. AAPS J. 2017; 19(2): 377-85, each of which is incorporated herein by reference in its entirety. Such approaches will be explored in future work.

Example 2 is focused primarily on testing the feasibility of using TRAAbs to treat cancer. If successful, future studies will be aimed at humanizing the pAbBD-scFv construct or developing alternative methods to create TRAAbs that are less likely to induce an immunogenic response.

Example 3: Optimize the Composition of Bispecifc T Cell-Redirecting Autoantibodies (TRAAbs)

Autoantibodies isolated from mice that have been vaccinated with breast cancer cells will be transformed into TRAAbs. Anti-CD3 single-chain variable fragments (scFv) will be used to confer specificity for T cells.

TRAAbs will be prepared using three different anti-CD3 scFvs (OKT-3, UCHT1, and SP34) and three different linker lengths between the antibody and scFv. In particular, five different anti-CD3 scFv constructs will be studied, three with scFvs against unique CD3 epitopes (OKT-3, UCHT1, and SP34) and two additional OKT-3 scFv constructs with different linker lengths between the scFv and IgG, as shown in Table 1.

TABLE 1

Summary of anti-CD3 scFvs

| scFv Origin | Linker | Specificity |
| --- | --- | --- |
| OKT3 | $(GGS)_2$ | CD3εγ and CD3εδ |
| OKT3 | $(GGS)_3$ | CD3εγ and CD3εδ |
| OKT3 | $(GGS)_5$ | CD3εγ and CD3εδ |
| UCHT1 | $(GGS)_3$ | CD3εγ and CD3εδ |

The biophysical properties (i.e., solubility, stability, tendency to form aggregates) of each TRAAb will be evaluated and also taken into consideration when selecting an optimal formulation. TRAAbs will also be characterized in terms of their antigen-specific T-cell mediated cytotoxicity. The TRAAb composition that exhibits maximal potency in a T cell-mediated cell lysis assay will be evaluated and identified. These findings will be used to select the optimal TRAAb composition.

Construction of pAbBD-scFv Fusions:

It has been shown that epitope selection can significantly affect the potency of target cell lysis with Babs, as described by Bluemel C, et al., Epitope distance to the target cell membrane and antigen size determine the potency of T cell-mediated lysis by BiTE antibodies specific for a large melanoma surface antigen. Cancer Immunol Immunother. 2010; 59(8):1197-209; and Jacobs N, et al., Efficiency of T cell triggering by anti-CD3 monoclonal antibodies (mAb) with potential usefulness in bispecific mAb generation. Cancer Immunol Immunother. 1997; 44(5):257-64, each of which is incorporated herein by reference in its entirety. Therefore, the cytolytic potency of TRAAbs that are formed using three different anti-CD3 scFvs: OKT3, UCHT1, or SP34 will be tested. The scFvs will be fused to the c-terminus of photoreactive Protein G-A24 via a $(GGS)_3$ linker. These particular scFvs were selected because they offer unique specificity, as described by Salmeron et al., A conformational epitope expressed upon association of CD3-epsilon with either CD3-delta or CD3-gamma is the main target for recognition by anti-CD3 monoclonal antibodies. J Immunol. 1991; 147(9):3047-52, which is incorporated herein by reference in its entirety, and the inventors were able to validate the amino acid sequences from at least three sources.

Since there are conflicting data on whether linker length has an effect on the efficacy of cell lysis, as described in Le Gall et al., Effect of linker sequences between the antibody variable domains on the formation, stability and biological activity of a bispecific tandem diabody. Protein Eng Des Sel. 2004; 17(4):357-66; and Mack et al., A small bispecific antibody construct expressed as a functional single-chain molecule with high tumor cell cytotoxicity. Proc Natl Acad Sci 1995; 92(15):7021-5, each of which is incorporated herein by reference in its entirety, two additional pAbBD-scFv fusions are created with linker lengths of $(GGS)_2$ and $(GGS)_5$ between the pAbBD and the OKT3 scFv. If T cell-mediated cell lysis is found to depend on linker length, additional linker lengths are tested and/or various linker lengths with the other anti-CD3 scFvs are tested. The preliminary data above were generated using the fusion protein pAbBD-$(GGS)_3$-OKT3 scFv.

Figures 9A, 9B, 9C:
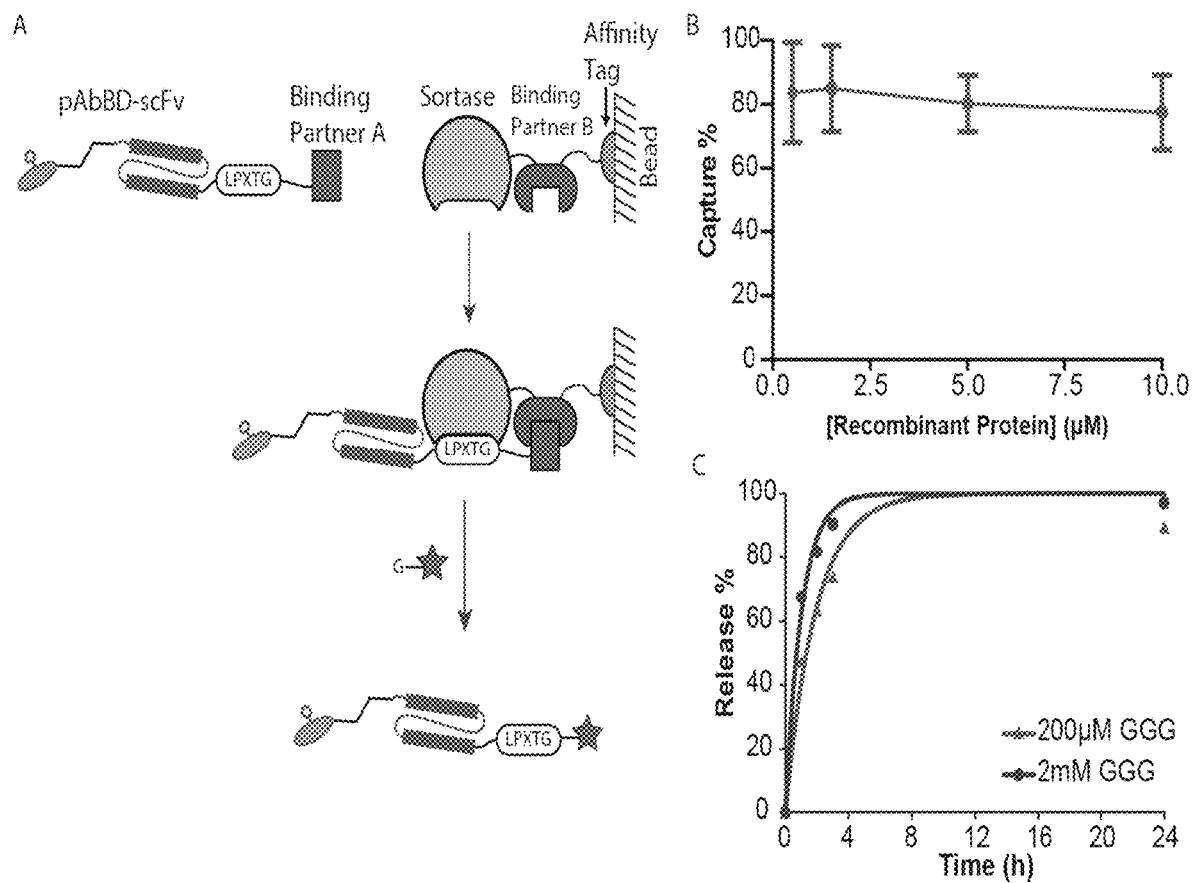
FIGS. 9A-9C.

The pAbBD-scFv fusion proteins will be expressed in our Proximity-Based Sortase Ligation (PBSL) system (FIG. 9A), as described by Wang H H, Altun B, Nwe K, Tsourkas A. Proximity-Based Sortase-Mediated Ligation. Angew Chem Int Ed Engl. 2017; 56(19):5349-52, which is incorporated herein by reference in its entirety. PBSL provides the flexibility to site-specifically label the C-terminus of the pAbBD-scFV with nearly any chemical moiety (e.g. biotin, fluorescent dye, etc.). Even when no label is introduced, PBSL still allows proteins to be isolated with significantly higher purity than conventional purification systems due to the very mild, sortase-mediated elution conditions (i.e. calcium and triglycine). The pAbBD-$(GGS)_3$-OKT3 scFv that has already been created is produced using our PBSL system.

Production and Purification of Anti-Tumor Autoantibodies:

To maximize the production of autoantibodies, C57BL/6 J mice will be vaccinated with mitomycin C-treated human MDA-MB-468 human breast cancer cells that have been engineered to overexpress EGFR. Starting at the sixth week of age, C57BL/6 J mice will enter a vaccination protocol consisting of 4-week cycles. During the first 2 weeks, mice will receive four twice-weekly i.p. vaccinations with $2\times10^6$ mitomycin C-treated cells in 0.4 ml of PBS, followed by 2 weeks of rest. The vaccination cycles will repeated twice. Then, the mouse blood will be collected by cardiac puncture and centrifuged. Autoantibodies in the serum will then be purified using Protein G beads. Based on prior experience, the inventors expect that ten C57BL/6 J mice (n=10) will be needed to complete all of the biophysical and T cell-mediated cell lysis studies. An equivalent number of unvaccinated (wild-type) C57BL/6 J mice (n=10) will be needed for controls.

Production of TRAAbs:

The five pAbBD-scFv variants will each be crosslinked to autoantibodies from vaccinated mice or control antibodies from wild-type mice, as previously described by Hui J Z, et al., A. Facile method for the site-specific, covalent attachment of full-length IgG onto nanoparticles. Small. 2014; 10(16):3354-63; and Hui J Z, Tsourkas A. Optimization of photoactive protein Z for fast and efficient site-specific conjugation of native IgG. Bioconjug Chem. 2014; 25(9): 1709-19, ehc of which is incorporated by refrence in its entirety. The reaction products will be analyzed on a reducing and non-reducing PAGE to confirm specific labeling of the heavy chains. Unconjugated pAbBD-scFvs will be removed using ultrafiltration spin columns (100 kDa MWCO, Millipore). Filtration will be conducted using Protein A/G elution buffer, to ensure only covalently bound pAbBD-scFv remains in the retentate. After washing, samples will be returned to PBS, pH 7.4. Purity of the TRAAbs will be evaluated by PAGE, FPLC, and mass spectrometry.

Size Variant Analysis of TRAAbs:

Since the formation of antibody aggregates can influence antibody performance, as described by Rosenberg A S, Worobec A. A risk-based approach to immunogenicity concerns of therapeutic protein products, Part 1: Considering consequences of the immune response to a protein. Biopharm Intl. 2004; 19:22-6; and Rosenberg A S, Worobec A. A risk-based approach to immunogenicity concerns of therapeutic protein products, Part 2: Considering host-specific and product specific factors impacting immunogenicity. Biopharm Intl. 2004; 19:34-42, each of which is incorporated herein by reference in its entirety, a size variant analysis will be performed on all TRAAbs and the corresponding unmodified autoantibodies. To assess aggregate formation, size exclusion chromatography will be conducted using an elution buffer containing 25% propylene glycol, which helps prevent non-specific interactions with the column stationary phase, as described by Hollander I, Kunz A, Hamann P R. Selection of reaction additives used in the preparation of monomeric antibody-calicheamicin conjugates. Bioconjug Chem. 2008; 19(1):358-61, which is incorporated herein by reference in its entirety. Aggregate formation will be evaluated as a function of storage time (up to 30 days). The PROTEOSTAT® protein aggregation assay and dynamic light scattering will also be used to study aggregation.

Biophysical Analysis of BAb Stability and Solubility:

To study the conformational stability of each TRAAb and the corresponding unmodified autoantibodies, a thermal analysis, i.e., differential scanning calorimetry (DSC), will be performed, as described by Wakankar A A, et al., Physicochemical stability of the antibody-drug conjugate Trastuzumab-DM1: changes due to modification and conjugation processes. Bioconjug Chem. 2010; 21(9):1588-95, which is incorporated herein by reference in its entirety. Poor thermal stability can affect the solubility of proteins and lead to aggregation, as described by Christ D, Famm K, Winter G. Repertoires of aggregation-resistant human antibody domains. Protein Eng Des Sel. 2007; 20(8):413-6; Famm K, et al., Thermodynamically stable aggregation-resistant antibody domains through directed evolution. J Mol Biol. 2008; 376(4):926-31; and Hmila I, et al., VHH, bivalent domains and chimeric Heavy chain-only antibodies with high neutralizing efficacy for scorpion toxin AahI'. Mol Immunol. 2008:45(14):3847-56, each of which is incorporated herein by reference in its entirety. A differential scanning calorimeter is available for these studies.

To assess solubility of each TRAAb and the corresponding unmodified IgG, hydrophobic interaction chromatography (HIC) will be performed. HIC is performed under non-denaturing conditions at neutral pH with a gradient from high salt to low salt. The retention time will provide insight into whether the pAbBD-scFv has any effect on hydrophobicity. Less hydrophobic antibodies will elute earlier on the HIC column, as described by Lienqueo et al., New approaches for predicting protein retention time in hydrophobic interaction chromatography. J Mol Recognit. 2006; 19(4):260-9; Lenhoff. Hydrophobic interaction chromatography of proteins. I. The effects of protein and adsorbent properties on retention and recovery. J Chromatogr A. 2007; 1141(2):191-205; and Wu et al., Site-specific chemical modification of recombinant proteins produced in mammalian cells by using the genetically encoded aldehyde tag. Proc Natl Acad Sci USA. 2009; 106(9):3000-5, each of which is incorporated herein by reference in its entirety.

As a secondary measure of solubility, cross-interaction chromatography (CIC) is done, as described in Jacobs et al., Cross-interaction chromatography: a rapid method to identify highly soluble monoclonal antibody candidates. Pharm Res. 2010; 27(1):65-71, which is incorporated herein by reference in its entirety. Briefly, IgG from human serum (Sigma) is chemically coupled to a HiTrap NHS-activated column (GE Healthcare). CIC retention times for each TRAAb and corresponding unmodified autoantibody is determined using a PBS mobile phase. Retention times are also determined on a control (no antibody coupled, hydrolyzed NHS) column.

Evaluating T Cell-Mediated Cell Lysis and Antibody-Dependent Cellular Cytotoxicity (ADCC):

To assess the antigen-specific T cell-mediated cytotoxicity of each TRAAb, cell lysis of EGFR-overexpressing MDA-MB-468 human breast cancer cells (target cells) is examined in the presence of human T cells (obtained from the Univ. of Pennsylvania Human Immunology Core).

To assess ADCC and non-specific T cell activation, analogous studies are done with native autoantibodies, anti-CD3 scFvs and mixtures of the two, as well as TRAAbs that were prepared using antibodies from wild-type mice. The same studies are done with autoantibody-pAbBD conjugates (no scFv) and mixtures of autoantibodies-pAbBD and anti-CD3 scFvs, to assess the impact of the pAbBD on ADCC. Additional control studies are done in the absence of T cells.

For comparison, cell lysis studies are also performed using anti-EGFR (cetuximab)×anti-CD3 BAbs, as described above.

For each study described above, cell lysis is measured as a function of antibody concentration (0.1 to 10,000 pM) and at different effector-to-target ratios (1:1 to 50:1). Cell lysis is monitored in real-time for up to 48 hours using an xCELLigence system (ACEA Biosciences).

Statistics:

For all cellular assays, dose response curves and $EC_{50}$ values are determined using four-parameter curve fitting. Statistical significance between groups is determined by analysis of variance (ANOVA) or a Student's t-test where appropriate. A $p<0.05$ is considered statistically significant.

Selection of Optimal TRAAb Composition:

The anti-CD3 scFv and linker that leads to the lowest $EC_{50}$ in T cell-mediated cell lysis assays will be used for all subsequent studies, barring no significant signs of aggregation or other biophysical properties that may interfere with their use.

Five unique TRAAbs with >90% purity are expected to be produced, from which an optimal TRAAb composition, with an $EC_{50}$<75 pM (at 12 hrs post-treatment), will be identified.

Alternative Studies:

Based on the preliminary studies described herein and extensive experience with scFv expression and purification, the inventors do not expect any major difficulties with expressing pAbBD-scFv fusion proteins; however, if there are particular pAbBD-scFv fusion proteins that cannot be expressed or if yield is low, a range of different *E. coli* cell lines (e.g. Origami, T7 Express, T7 Shuffle, etc.) and conditions will first be evaluated.

If sufficient protein expression is still not obtained, an attempt to express the protein in yeast or CHO cells will be made. It has already been demonstrated that the pAbBD-OKT3 scFv can be produced in yeast, using a mutant *E. coli* aminoacyl-tRNA synthetase in combination with an amber suppressor tRNA from *Bacillus stearothermophilus*, as previously described by Liu W, Brock A, Chen S, Chen S, Schultz P G. Genetic incorporation of unnatural amino acids into proteins in mammalian cells. Nat Methods. 2007; 4(3):239-44, which is incorporated herein by reference in its entirety. Notably, PBSL is also compatible with proteins expressed in yeast.

Based on the preliminary data described herein and because of the similarity in structure, it is not expected that the crosslinking efficiency between autoantibodies and any of the pAbBD-scFv constructs will be low; however, if it is lower than expected (i.e. <95%), longer exposures to UV light for photocrosslinking, higher reaction concentrations, or higher pAbBD:IgG labeling ratios can be tested.

A TRAAb composition with an $EC_{50}$ that is half of the current formulation is expected to be identified, i.e. 75 pM, but if necessary, the current composition is expected to be sufficient for subsequent tests.

Example 4: Evaluate the Therapeutic Potential of TRAAbs Formed from Autoantibodies Isolated from Three Distinct Transgenic Murine Breast Cancer Tumor Models The enrichment of autoantibodies in tumor tissue is assessed using three different genetically engineered mouse models of breast cancer that resemble human disease. This is done by immunostaining for the presence of IgG on tumor tissue and quantifying the extent of labeling. In addition to studying the tumor tissue, autoantibodies are also isolated at different disease stages and their cytolytic potential will be evaluated in culture, i.e., $EC_{50}$, in T cell-mediated cell lysis assays. This provides insight into the enrichment of anti-tumor autoantibodies in serum as a function of disease progression. Next, the pharmacokinetics of TRAAbs is determined. A dose-ranging study is performed to approximate the TRAAB dose required to promote a tumor response in human T cell engrafted immunodeficient mice. Immunodeficient mice are required to test therapeutic efficacy since the proposed TRAAb formulations possess anti-human CD3 scFvs and thus human T cells must be utilized, which would be immunogenic in immune competent mice. The effect of TRAAbs on T cell recruitment to tumors and the functionality of infiltrating T cells will be assessed. The extent of metastatic disease also will be quantified.

A quick calculation suggests that TRAAb therapy is feasible. Specifically, in mice, the serum concentration of immunoglobulin G is between 2 and 5 mg/mL, as described in Typical Immunoglobulin Concentration Ranges Normal Sera: Sigma-Aldrich. (Available from the Sigma-Aldrich website), which is incorporated herein by reference in its entirety. Therefore, 100 µL of serum would provide at least 0.2 mg of antibody. If half is lost during processing, there would be about 0.1 mg of TRAAb available for administration back into the patient. For an average mouse that weights 20 g, this would amount to a dose of 5 mg/kg. A survey of the literature suggests that a bispecific antibody dose of ≤1 µg per mouse (0.05 mg/kg) is sufficient to obtain a significant therapeutic effect in solid tumors, as described by Lutterbuese et al., T cell-engaging BiTE antibodies specific for EGFR potently eliminate KRAS- and BRAF-mutated colorectal cancer cells. Proc Natl Acad Sci USA. 2010; 107(28):12605-10; .Root A R, et al., Development of PF-06671008, a Highly Potent Anti-P-cadherin/Anti-CD3 Bispecific DART Molecule with Extended Half-Life for the Treatment of Cancer. Antibodies. 2016; 5(1); and Taki S, et al., A Novel Bispecific Antibody against Human CD3 and Ephrin Receptor A10 for Breast Cancer Therapy. PLoS One. 2015:10(12):e0144712, each of which is incorporated herein by reference in its entirety. These calculations suggest that for a 5 mg/kg dose, at least 1% of the injected TRAAbs must be active against tumor antigens to achieve an 'effective dose' of 0.05 mg/kg.

Based on the preliminary studies described herein (see Example 2), the $EC_{50}$ of TRAAbs, produced using autoantibodies from mice vaccinated with tumor cells, is approximately 150 pM, compared to 50 pM for a homogeneous bispecific antibody formulation with specificity for a single antigen on the same tumor cells, in a T cell-mediated cell lysis assay. From this data, it can be 'loosely' inferred that about 33% of the TRAABs are active against tumor antigens in this model. The studies described herein are expected to determine potency of TRAAbs that have been isolated from tumor models that more closely resemble human disease and at various stages of tumor progression and evaluate whether they can be used to effectively treat these same tumors in mice.

Notably, in humans, the serum IgG concentration is between 7.5 to 22 mg/mL. Therefore, 60 mL of serum (~¼ pint of blood) would provide at least 900 mg of antibody. If half is lost during processing, about 450 mg of TRAAb would be available to administer back into the patient. For an average male patient of 90 kg, this amounts to a dose of 5 mg/kg. For reference, the cumulative dose for the bispecific antibodies Catumaxomab and Blinatunimab is ~250 µg (0.003 mg/kg) and ~7.5 mg (0.08 mg/kg-assuming 9 cycles), respectively. Therefore, assuming a therapeutic dose of 5/mg/kg, only 0.06% to 1.6% of the TRAAbs would need to be active against tumor antigens.

While TRAAbs induced immune-related adverse events (irAEs) are possible, it should be noted that both checkpoint inhibitor therapy and TILs face a similar challenge, since both of these approaches also involve broad antigen recognition. The success of these therapies suggests that any observed irAEs would be manageable. In fact, for the anti-CTLA-4 checkpoint inhibitor, ipilimumab, general guidelines for the management of irAEs are incorporated in the FDA Risk Evaluation and Management Strategies. A similar approach would likely apply for TRAAbs.

Mouse Models:

Three genetically engineered mouse models (GEMMs) for breast cancer will be utilized to produce anti-tumor antibodies, MMTV-rtTA;TetO-HER2/neu (MTB/HER2), MMTV-rtTA;TetO-Wnt1 (MTB/Wnt1) and MMTV-rtTA; TetO-Cre;p53$^{flox/flox}$ (MTB/TTC1/p53). The MTB, TetO-HER2, TetO-Wnt1 and TetO-Cre transgenic mouse lines were generated and characterized. In the MTB/HER2 and MTB/Wnt1 GEMM, the tetracycline regulatory system is used to conditionally express activated HER2 or Wnt1 in the mammary epithelium, as described by Boxer R B, Stairs D B, Dugan K D, Notarfrancesco K L, Portocarrero C P, Keister B A, Belka G K, Cho H, Rathmell J C, Thompson C B, Birnbaum M J, Chodosh L A. Isoform-specific requirement for Akt1 in the developmental regulation of cellular metabolism during lactation. Cell Metab. 2006; 4(6):475-90. D'Cruz C M, Gunther E J, Boxer R B, Hartman J L, Sintasath L, Moody S E, Cox J D, Ha S I, Belka G K, Golant A, Cardiff R D, Chodosh L A. c-MYC induces mammary tumorigenesis by means of a preferred pathway involving spontaneous Kras2 mutations. Nat Med. 2001; 7(2):235-9; Gunther E J, et al., A novel doxycycline-inducible system for the transgenic analysis of mammary gland biology. FASEB J. 2002:16(3):283-92; Gunther E J, et al., Impact of p53 loss on reversal and recurrence of conditional Wnt-induced tumorigenesis. Genes Dev. 2003; 17(4):488-501; Jang J W, et al., Isoform-specific ras activation and oncogene dependence during MYC- and Wnt-induced mammary tumorigenesis. Mol Cell Biol. 2006:26(21):8109-21; Moody S E, et al., Conditional activation of Neu in the mammary epithelium of transgenic mice results in reversible pulmonary metastasis. Cancer Cell. 2002; 2(6):451-61; Sarkisian et al., Dose-dependent oncogene-induced senescence in vivo and its evasion during mammary tumorigenesis. Nat Cell Biol. 2007; 9(5):493-505; Slamon D J, et al., Human breast cancer: correlation of relapse and survival with amplification of the HER-2/neu oncogene. Science. 1987; 235(4785):177-82; and Slamon et al., Studies of the HER-2/neu proto-oncogene in human breast and ovarian cancer. Science. 1989; 244(4905):707-12, each of which is incorporated by reference in its entirety.

Following oncogene induction with doxycycline, mice develop invasive mammary tumors that spontaneously metastasize to the bone marrow, lungs, liver, lymphatics and brain-sites characteristically found in patients with breast cancer, as described by Baselga J, et al., Lapatinib with trastuzumab for HER2-positive early breast cancer (NeoALTTO): a randomised, open-label, multicentre, phase 3 trial. Lancet. 2012; 379(9816):633-40; Doyle T, et al., Long-term results of local recurrence after breast conservation treatment for invasive breast cancer. Int J Radiat Oncol Biol Phys. 2001; 51(1):74-80; Fisher B, et al., Significance of ipsilateral breast tumour recurrence after lumpectomy. Lancet. 1991:338(8763):327-31; Fortin A. et al., Local failure is responsible for the decrease in survival for patients with breast cancer treated with conservative surgery and postoperative radiotherapy. J Clin Oncol. 1999; 17(1):101-9; Schmoor et al., Role of isolated locoregional recurrence of breast cancer: results of four prospective studies. J Clin Oncol. 2000; 18(8): 1696-708, each of which is incorporated by reference in its entirety. Tumor are clonal, arise with long latency, have a luminal phenotype similar to ER+ tumors in humans, and harbor >20 coding mutations per tumor, similar to that found in human breast cancers, as well as frequent amplifications and deletions. Thus, GEMM tumors—like their human counterparts—are genomically complex, driven by similar oncogenic pathways, and metastasize to similar sites. Notably, primary tumors in GEMMs treated by inhibiting oncogene expression or activity undergo dramatic regression, but leave behind small populations of residual tumor cells (RTCs) that can spontaneously give rise to recurrent tumors at local and distant sites. Analogously, treatment of HER2-amplified breast cancers in patients with HER2 targeted agents results in dramatic tumor regression, as described by, for example, Baselga et al., Lancet. 2012; 379(9816):633-40; and Robidoux et al., Lapatinib as a component of neoadjuvant therapy for HER2-positive operable breast cancer (NSABP protocol B-41): an open-label, randomised phase 3 trial. Lancet Oncol. 2013; 14(12):1183-92, each of which is incorporated by reference in its entirety.

In the MTB/TTC1/p53 GEMM, the tetracycline regulatory system is used to conditionally express Cre, which triggers biallelic p53 deletion in the mammary epithelium that ultimately leads to the development of tumors with features characteristic of advanced human malignancies, including undifferentiated histology, genetic instability, and aneuploidy, as described by Donehower et al., Deficiency of p53 accelerates mammary tumorigenesis in Wnt-1 transgenic mice and promotes chromosomal instability. Genes Dev. 1995; 9(7):882-95; and Donehower et al., The role of p53 loss in genomic instability and tumor progression in a murine mammary cancer model. Prog Clin Biol Res. 1996; 395:1-11, each of which is incorporated by reference in its entirety.

Moreover, p53 loss facilitates tumor escape from therapy and the acquisition of oncogene independence, as described in Gunther et al., Impact of p53 loss on reversal and recurrence of conditional Wnt-induced tumorigenesis. Genes Dev. 2003; 17(4):488-501, which is incorporated herein by reference in its entirety. The selected GEMMs faithfully recapitulate key stages of breast cancer progression, including minimal residual disease, tumor dormancy and recurrence.

Immunostaining and Histological Examination of Tissues:

Approximately 6-week old MTB/HER2 mice (n=12) are treated with a low dose of doxycycline (0.1 mg/mL) to induce invasive mammary carcinomas. Groups of five mice are sacrificed at 4, 8, 12 and 16 weeks post-induction. Mouse blood is collected by cardiac puncture at each time point and autoantibodies are isolated from serum using Protein G beads. Mammary glands, lungs, liver, spleen, bladder, heart, kidneys, and brain are harvested, formalin fixed and paraffin embedded. Tissue and blood are also acquired from control MTB/HER2 mice (n=3) that were not treated with doxycycline. Tissue sections are stained with a secondary biotinylated horse anti-mouse IgG, followed by Streptavidin-HRP and Tyramide-Alexa Fluor 488, as described by Rich et al., Endogenous antibodies for tumor detection. Sci Rep. 2014; 4:5088, which is incorporated herein by reference in its entirety. To determine if anti-IgG staining is associated with infiltrating immune cells, sections are also stained for Iba-1 (macrophage marker) and CD45R (B cell marker). Adjacent sections are H&E stained. To evaluate the degree of non-specific secondary antibody binding, additional negative controls are done using biotinylated secondary anti-rabbit IgG. All sections are counterstained with DAPI. A veterinary pathologist (Penn Comparative Pathology Core), blinded to treatment groups, examines all H&E stained tissue sections. All histologically abnormal sections are marked and graded according to their degree of abnormality.

Analogous studies are performed with doxycycline-treated MTB/Wnt1 (n=12) and MTB/TTC1/p53 mice (n=12) and the corresponding untreated control MTB/Wnt1 (n=3) and MTB/TTC1/p53 mice (n=3).

Imaging and Statistical Analysis of Immunofluorescence:

Whole slides containing tissue sections are imaged using a Vectra Automated Quantitative Pathology Imaging System, which is available through the Pathology Clinical Service Center at Penn. Image analysis is done as described by Rich et al., Endogenous antibodies for tumor detection. Sci Rep. 2014; 4:5088, which is incorporated herein by reference in its entirety. Briefly, intensity histograms, normalized to tissue area, are plotted. A comparison between groups is done on the top 60% of intensities using a Mann-Whitney U test, which does not require an assumption of normal distributions. A $p<0.05$ is considered statistically significant.

In addition to quantification of total integrated fluorescence, the pattern of fluorescence is also examined by confocal microscopy. This provides insight into the tumor sub-regions where anti-tumor autoantibodies reside, e.g. stroma, core, etc.

Evaluation of T Cell-Mediated Cell Lysis:

Autoantibodies purified from GEMMs serum are cross-linked with the optimum pAbBD-scFv construct to create TRAAbs, and are validated by SDS-PAGE. T cell-mediated cytolysis assays are then done, as described in Example 3, but with primary tumor cells isolated from the MTB/HER2 (n=12), MTB/Wnt1 (n=12), and MTB/TTC1/p53 mice (n=12) that are sacrificed at 4, 8, 12 and 16 weeks, post-induction with doxycycline. As a positive control for the MTB/HER2 model, cell lysis studies are performed using anti-HER2×anti-CD3 BAbs. BAbs constructed with anti-Her2 and anti-EGFR antibodies are tested as positive controls for the MTB/Wnt1 and MTB/TTC1/p53 models. The $EC_{50}$ is determined and compared as described in Example 3.

To model a scenario of antigen loss, an additional T cell-mediated cell lysis assay is done with primary MTB/HER2 cells cultured in the absence of doxycycline. The loss of Her2 makes the cells insensitive to treatment with the anti-HER2×anti-CD3 BAb, but these cells are expected to remain sensitive to TRAAb treatment.

Selection of GEMM for Dosing Study:

The GEMM that produces TRAAbs with the lowest $EC_{50}$ at 16 weeks are used for subsequent dose-ranging studies.

Pharmacokinetics of TRAAbs:

A cohort of ten (n=10) 3-6 month old C57BL/6 J mice are injected intravenously with biotinylated TRAAbs (5 mg/kg) on day 0 (d0) and blood is collected at 1 week prior to antibody injection, immediately following injection, 1 hr, 4 hr, 1 day, 4 days, 1 week, 2 weeks, and 1 month post-injection. TRAAbs are biotinylated via PBSL, as described in Example 3. The TRAAbs are detected at different dilutions of serum using an ELISA with streptavidin and a standard curve with different amounts of TRAAb diluted into pooled unmanipulated B6 mouse sera. Analogous studies are performed with biotinylated autoantibodies, from which the TRAAbs were derived (n=10 mice total). The autoantibodies will have their lysines labeled with NHS-biotin.

Dose-Ranging Study:

A dose-ranging study is performed using a 4-log range of TRAAbs to determine the approximate dose needed to promote an anti-tumor response (increase in median survival, slowed tumor growth) in human T cell engrafted immunodeficient mice. TRAAbs are prepared using autoantibodies isolated from genetically engineered mice (n=60) that were induced with doxycycline at approximately 6-weeks of age and sacrificed at 16-weeks post-induction. Primary tumor cells are also isolated from the sacrificed mice and expanded in culture, in the presence of doxycycline. TRAAbs are also prepared using autoantibodies isolated from genetically engineered mice (n=10) that were not induced with doxycycline.

The primary tumor cells ($2.5 \times 10^6$) are implanted orthotopically into NOD/scid/$\gamma_c^{-/-}$ (NSG) mice (n=50). Once the tumors reach a size of ~5 mm, mice receive an i.p. injection of $2 \times 10^7$ activated/expanded T cells as a source of effector T cells. Mice from each condition are randomly placed into 5 TRAAb dose groups (PBS-only, 0.05 mg/kg, 0.5 mg/kg, 5 mg/kg, and 50 mg/kg; n=10 mice/group), which is delivered i.v. over the course of 5 days (one injection per day). TRAAbs administration begins two days after T cell injection. Mice are evaluated daily for weight, activity, well-being, and overall survival via Kaplan-Meier analyses. A log-rank analysis is performed on data in Kaplan-Meier curves to identify statistical significance ($p<0.05$) between groups. Tumor growth is measured with a caliper and tumor volume is calculated using an ellipsoid formula. At time of sacrifice, mammary glands, lungs, liver, spleen, bladder, heart, kidneys, and brain are harvested. Control studies are performed with untreated mice (n=10).

Using the lowest dose for TRAAbs (with T cells) that results in tumor regression to a non-palpable state, additional control studies include: i) Mice injected with TRAAbs, but not T cells (n=10); ii) Mice injected with autoantibodies from tumor bearing mice, with T cells (n=10 mice) and iii) mice injected with TRAAbs prepared using autoantibodies from non-tumor-bearing mice, with T cells (n=10 mice). If no TRAAb dose results in complete eradication of the tumor, control studies are performed at the maximum antibody dose (50 mg/kg).

Tissue Analysis:

The weight and volume of resected tissue specimens are recorded. Half of the tumor tissue is used to quantify major lymphocyte lineages by flow cytometry, while the other half is formalin fixed and paraffin embedded for immunostaining and histological examination of T cell distribution. Flow cytometry is used to identify the populations of CD4+ and CD8+ T cells, and CD19+ B cells. The percentage of each population is based on identification of all hematopoietic cells (CD45+). The ratio of CD4/CD8 cells is also calculated. Cells are also labeled for CD45R to allow for differentiation of naïve and memory T cells.

To quantify metastatic burden in each tissue, half of each tissue is analyzed for the presence of the transgene, at the DNA level, by quantitative RT-PCR, as described by Abt et al., Evaluation of Lung Metastasis in Mouse Mammary Tumor Models by Quantitative Real-time PCR. J Vis Exp. 2016(107):e53329, which is incorporated herein by refrence in its entirety. The other half is formalin fixed and paraffin embedded for histological examination.

Immunostaining and histological examination of all tissues is carried out as described above, but with additional stains to identify T cell populations within the tumor. A veterinary pathologist (Penn Comparative Pathology Core), blinded to the treatment groups, examines all H&E stained tissue sections. All histologically abnormal sections are marked and graded according to their degree of abnormality and extent of metastatic disease.

These studies expect to confirm enrichment of autoantibodies in tumors in the three GEMMs, to confirm that TRAAbs are able to trigger T cell-mediated killing of primary tumor cells, to show that T cell-mediated killing of primary MTB/HER2 cells with TRAAbs is not sensitive to antigen loss, following removal of doxycycline, and to show a dose-dependent anti-tumor effect of TRAAbs in a GEMM.

Alternative Studies:

Considering that as much as a 64-fold enrichment of autoantibodies has already been observed in three disparate GEMMs and that some level of enrichment was observed in every case, as described by Rich et al., Sci Rep. 2014; 4:5088, which is incorporated by reference in its entirety, similar phenomena is expected to be observed in the GEMMs that are tested. A lack of enrichment in all three GEMMs would therefore likely represent poor immunostaining, which can be resolved by selecting different antibodies for IgG staining or optimizing the staining protocol. If TRAAbs are not able to trigger T cell-mediated cell killing in culture, higher doses are tried initially. Tumor-specific autoantibodies can also potentially be enriched by adopting some of the same strategies that are being tested for personalized cancer vaccines, e.g. whole tumor cell-based vaccines, as described by Bencherif S A, et al., Injectable cryogel-based whole-cell cancer vaccines. Nat Commun. 2015; 6:7556; de Gruijl T D, et al., Whole-cell cancer vaccination: from autologous to allogeneic tumor- and dendritic cell-based vaccines. Cancer Immunol Immunother. 2008; 57(10):1569-77; Hu Z, et al., Towards personalized, tumour-specific, therapeutic vaccines for cancer. Nat Rev Immunol. 2017; Keenan B P, Jaffee E M. Whole cell vaccines—past progress and future strategies. Semin Oncol. 2012; 39(3):276-86; and Xia L, et al., Whole-Cell Cancer Vaccines Induce Large Antibody Responses to Carbohydrates and Glycoproteins. Cell Chem Biol. 2016; 23(12): 1515-25, each of which is incorporated herein by refrence in its entirety.

In particular, animals are vaccinated with (autologous) primary tumor cells that have been irradiated or lysed. If necessary, the immune response is further enhanced by engineering the primary cancer cells to express GM-CSF, as described by Dranoff et al., Vaccination with irradiated tumor cells engineered to secrete murine granulocyte-macrophage colony-stimulating factor stimulates potent, specific, and long-lasting anti-tumor immunity. Proc Natl Acad Sci 1993; 90(8):3539-43; Ho et al., Biologic activity of irradiated, autologous, GM-CSF-secreting leukemia cell vaccines early after allogeneic stem cell transplantation. Proc Natl Acad Sci 2009; 106(37):15825-30; and Jaffee et al., Novet allogeneic granulocyte-macrophage colony-stimulating factor-secreting tumor vaccine for pancreatic cancer: a phase I trial of safety and immune activation. J Clin Oncol. 2001:19(1):145-56, each of which is incorporated herein by reference in its entirety. A related vaccination approach is already being explored in a Phase II clinical trial (NCT01773395) to treat MDS/CMML/AML, which is incorporated herein by reference in its entirety. The inventors have already shown that TRAAbs can be produced with an effective $EC_{50}$ of 150 pM when adopting a vaccination protocol to trigger an immune response. Tumor cell-based vaccines are also used to stimulate autoantibody production if no anti-tumor effects with TRAAbs in the dose-ranging study are observed. Another option is to co-inject T cells with the TRAAbs to improve the likelihood and efficiency of binding and redirecting of T cells.

Example 5: Evaluate the Efficacy of TRAAb Therapy in Combination with the Checkpoint Inhibitor, PDL1

This study evaluates whether TRAAbs enhance the potency of PDL1 therapy by aiding in the recruitment of more T cell into tumor tissue. Autoantibodies are isolated from mice that have been vaccinated with MDA-MB-231 and mice vaccinated with EGFR over-expressing MDA-MB-468 cells. Both MDA-MB-231 and MD-MB-468 are human triple negative breast cancer (TNBC) cells that express high levels of PDL1. After the autoantibodies are transformed in TRAAbs, a T cell-mediated cytolysis studies are done with varying doses of TRAAbs in combination with PDL1. Next, a dose-ranging study is done to approximate the TRAAb dose needed to promote a tumor response in human T cell engrafted immunodeficient mice. Sub-curative doses of TRAAb are combined with a PDL1 to assess the additive/synergistic effect. T cell recruitment and the functionality of infiltrating T cells are assessed. The extent of metastatic disease is also quantified.

Production and Purification of Anti-Tumor Autoantibodies and TRAAbs:

To maximize the production of autoantibodies, C57BL/6 J mice are vaccinated with mitomycin C-treated human MDA-MB-468 human breast cancer cells that have been engineered to overexpress EGFR or MDA-MB-231 cells, as described in Example 3. Based on prior experience, it is expected that twenty C57BL/6 J mice (n=20; 10 per cell line) are needed to complete all of the T cell-mediated cell lysis studies. An equivalent number of unvaccinated C57BL/6 J mice (n=20) are needed for controls.

Evaluation of T Cell-Mediated Cell Lysis:

Autoantibodies purified from the serum of the vaccinated mice are crosslinked with the optimum pAbBD-scFv construct to create TRAAbs, and are validated by SDS-PAGE. T cell-mediated cytolysis assays is then done using TRAAbs alone (as described in Example 3) or in combination with anti-PDL1 (10 µg/mL; BioXCell). Analogous studies are done with native autoantibodies, anti-CD3 scFvs and mixtures of the two, as well as TRAAbs prepared using antibodies from wild-type mice. Additional control studies are done in the absence of T cells. For comparison, cell lysis studies are also done using anti-EGFR (cetuximab)×anti-CD3 BAbs, as described above.

For each study described above, cell lysis is measured as a function of antibody concentration (0.1 to 10,000 pM) and at different effector-to-target ratios (1:1 to 50:1). Cell lysis is monitored in real-time for up to 48 hours using an xCELLigence system (ACEA Biosciences). The $EC_{50}$ values and statistical analysis are performed as described in Example 3. It is hypothesized that the $EC_{50}$ of TRAAbs is lower when combined with anti-PDL1.

Selection of Orthotopic Xenograft Model for Dosing Study:

The cell line that demonstrates the highest sensitivity to anti-PDL1 therapy (i.e., largest effect on $EC_{50}$) is used for subsequent dose-ranging studies.

Dose-Ranging Study:

A dose-ranging study is done using a 4-log range of TRAAbs to determine the approximate dose needed to promote an anti-tumor response (increase in median survival, slowed tumor growth) in human T cell engrafted immunodeficient mice. TRAAbs are prepared using autoantibodies isolated from vaccinated mice (n=70). TRAAbs prepared using autoantibodies are also isolated from wild-type mice (n=10) that were not subject to the vaccination protocol.

The PDL1-positive cells ($2.5 \times 10^6$) are implanted orthotopically into NOD/scid/lyc (NSG) mice (n=50). Once tumors reach a size of ~5 mm, the mice receive in i.p. injection of $2 \times 10^7$ activated/expanded T cells as a source of effector T cells. Mice from each condition are randomly placed into 5 TRAAb dose groups (PBS-only, 0.05 mg/kg, 0.5 mg/kg, 5 mg/kg, and 50 mg/kg; n=10 mice/group), which is delivered i.v. over the course of 5 days (one injection per day). TRAAbs administration begins two days after T cell injection. Mice are evaluated daily for weight, activity, well-being, and overall survival via Kaplan-Meier analyses. A log-rank analysis is performed on data in Kaplan-Meier curves to identify statistical significance ($p<0.05$) between groups. Tumor growth is measured with a caliper and tumor volume is calculated using an ellipsoid formula. At time of sacrifice, the mammary tissue, lungs, liver, spleen, bladder, heart, kidneys, and brain are harvested. Control studies are performed with untreated mice (n=10).

Using a dose for TRAAbs (with T cells) that elicits a tumor response, but is sub-curative, studies are then performed with mice (n=10) that receive both TRAAbs and anti-PDL1 (10 mg/kg). The anti-PDL1 is administered i.v. simultaneously with TRAAbs, i.e. over the course of 5 days.

Additional control studies include, i) Mice injected with TRAAbs and anti-PDL1, but not T cells (n=10); ii) mice injected with native autoantibodies from tumor bearing mice and anti-PDL1, with T cells (n=10 mice); iii) mice injected with TRAAbs prepared using autoantibodies from non-tumor-bearing mice and anti-PDL1, with T cells (n=10 mice).

Tissue Analysis:

Flow cytometric analysis, immunostaining and histological examination are performed as described in Example 4.

These studies expect to show that anti-PDL1 antibodies improve (lower) the T cell-mediated cytotoxicity ($EC_{50}$) of TRAAbs, show that anti-PDL1 antibodies are able to enhance the therapeutic efficacy of TRAAbs in an orthotopic xenograft model of breast cancer, and show that TRAAbs are able to aid in the recruitment of T cells to tumors.

Alternative Studies:

It has been shown that anti-PDL1 antibodies improve the T cell-mediated cytotoxicity of tumor-specific T cells in vitro, as described by Blank et al., Blockade of PD-L1 (B7-H1) augments human tumor-specific T cell responses in vitro. Int J Cancer. 2006; 119(2):317-27, which is incorporated herein by reference in its entirety; therefore, a similar trend is expected to be observed here. However, if this is not the case, higher doses of PDL1 is tried and anti-PD1 antibodies are tested, which will confirm that PD1 and PDL1 are being expressed on the T cells and cancer cells, respectively. Similar steps are taken if the anti-PDL1 antibodies do not enhance the therapeutic efficacy of TRAAbs in the xenograft model. If TRAAbs alone do not elicit a therapeutic response, similar steps can be taken as described in Example 4 to boost potency.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A bispecific cytotoxic lymphocyte or macrophage-redirecting autoantibody comprising a cytotoxic lymphocyte or macrophage targeting domain and an autoantibody isolated from the sera of a live tumor-bearing subject.

2. The bispecific cytotoxic lymphocyte or macrophage-redirecting autoantibody of claim 1, wherein the cytotoxic lymphocyte is a T cell or natural killer (NK) cell.

3. The bispecific cytotoxic lymphocyte or macrophage-redirecting autoantibody of claim 1, wherein the autoantibody is an Immunoglobulin G (IgG) molecule that is isolated from a living subject and is against a tumor, autoantigen, or foreign body, wherein the foreign body is a virus, bacteria, or parasite.

4. The bispecific cytotoxic lymphocyte or macrophage-redirecting autoantibody of claim 1, wherein the cytotoxic lymphocyte or macrophage targeting domain is an antibody or an antibody fragment, wherein the antibody is an Immunoglobulin G (IgG) and the antibody fragment is an Fc, a single chain Fv (scFv), an Fab, Fab', Fv, F(ab')$_2$, single domain antibody, monobody, or a Knottin.

5. The bispecific cytotoxic lymphocyte or macrophage-redirecting autoantibody of claim 4, wherein the cytotoxic lymphocyte or macrophage targeting domain is fused to a photoreactive antibody-binding domain (pAbBD), wherein the pAbBD contains a photoreactive crosslinker that is photoreactively conjugated to an autoantibody isolated from a living subject.

6. The bispecific cytotoxic lymphocyte or macrophage-redirecting autoantibody of claim 5, wherein the photoreactive crosslinker is the unnatural amino acid benzoyl-phenyl-alanine.

7. The bispecific cytotoxic lymphocyte or macrophage-redirecting autoantibody of claim 5, wherein the antibody-binding domain is derived from a thermally stable domain of Protein G (HTB1), wherein the Protein G domain comprises SEQ ID NO: 1.

8. The bispecific cytotoxic lymphocyte or macrophage-redirecting autoantibody of claim 2, wherein the T cell comprises a targeting domain that targets a CD3 receptor and/or the cytotoxic lymphocyte targeting domain is a NK cell targeting domain that targets a NK cell receptor CD16, CD16A, IPH61, NKG2D, NKp46, NKp30, or DNAM-1 and/or the macrophage targeting domain targets a macrophage receptor CD47, CD89 or CD16A.

9. The bispecific cytotoxic lymphocyte or macrophage-redirecting autoantibody of claim 4, wherein the scFv is an anti-CD3 scFv.

10. The bispecific cytotoxic lymphocyte or macrophage-redirecting autoantibody of claim 9, wherein the anti-CD3 scFv is an scFv of anti-human CD3 murine monoclonal antibody OKT-3 having a binding specificity for CD3εγ and CD3εδ;or the anti-CD3 scFv is an scFv of anti-human CD3 murine monoclonal antibody UCHT1 having a binding specificity for CD3εγ and CD3εγ and has a (GGS)$_3$ linker; or the anti-CD3 scFv is an scFv of anti-human CD3 murine monoclonal antibody SP34 having a binding specificity for CD3ε, CD3εγ and CD3εδ and has a (GGS)$_3$ linker.

11. The bispecific cytotoxic lymphocyte or macrophage-redirecting autoantibody of claim 5, wherein the scFv has a (GGS)$_2$ linker, a (GGS)$_3$ linker or a (GGS)$_5$ linker.

12. The bispecific cytotoxic lymphocyte or macrophage-redirecting autoantibody of claim 1, wherein the autoantibody is an immunoglobulin G (IgG).

13. The bispecific cytotoxic lymphocyte or macrophage-redirecting autoantibody of claim 12, wherein the IgG is a full-length human IgG.

14. The bispecific cytotoxic lymphocyte or macrophage-redirecting autoantibody of claim 1, which is trivalent or tetravalent.

15. A method for producing of a bispecific cytotoxic lymphocyte or macrophage-redirecting autoantibody, the method comprising:
    isolating an endogenous autoantibody from sera of a living subject having a tumor or foreign body;
    covalently conjugating the isolated endogenous autoantibody to a cytotoxic lymphocyte or macrophage targeting domain, wherein the cytotoxic lymphocyte or macrophage targeting domain is fused to a photoreactive antibody-binding domain (pAbBD), and the pAbBD contains a photoreactive crosslinker, that upon irradiating with long wavelength UV light covalently links the pAbBD and the cytotoxic lymphocyte or macrophage targeting domain to the isolated endogenous autoantibody, thereby producing the bispecific cytotoxic lymphocyte or macrophage-redirecting autoantibody.

16. The method of claim 15, wherein the cytotoxic lymphocyte is a T cell or natural killer (NK) cell.

17. The method of claim 15, wherein the cytotoxic lymphocyte or macrophage targeting domain is an antibody or an antibody fragment, wherein the antibody is an Immunoglobulin G (IgG) and the antibody fragment is an Fc, a single chain Fv (scFv), an Fab, Fab', Fv, F(ab')$_2$, affibody, nanobody, single domain antibody, monobody, or a Knottin.

18. The method of claim 16, wherein the T cell comprises a targeting domain that targets a CD3 receptor and/or the cytotoxic lymphocyte targeting domain is a NK cell targeting domain that targets a NK cell receptor CD16, CD16A, IPH61, NKG2D, NKp46, NKp30, or DNAM-1 and/or the macrophage targeting domain targets a macrophage receptor CD47, CD89 or CD16A.

19. The method of claim 17, wherein the scFv is an anti-CD3 scFv.

20. A method for treating a subject in need thereof comprising administering to the subject an isolated bispecific cytotoxic lymphocyte or macrophage-redirecting autoantibody comprising a cytotoxic lymphocyte or macrophage targeting domain photoreactively conjugated to an autoantibody isolated from a live tumor-bearing subject, wherein the antibody-binding domain comprises a photoreactive crosslinker.

21. The method of claim 20, wherein the subject has breast cancer.

22. The method of claim 20, further comprising administering to the subject an anti-Programmed Cell death protein ligand 1 (PDL1) antibody.

23. A therapeutic composition comprising a therapeutically effective dose of the bispecific cytotoxic lymphocyte or macrophage-redirecting autoantibody of claim 1.

24. The therapeutic composition of claim 23 wherein the therapeutically effective dose is about 0.05 $mg_{therapeutic}/kg_{patient}$ to about 50 $mg_{therapeutic}/kg_{patient}$.

25. The therapeutic composition of claim 24 wherein the therapeutically effective dose is about 0.05 $mg_{therapeutic}/kg_{patient}$.

26. The bispecific cytotoxic lymphocyte or macrophage-redirecting autoantibody of claim 1, wherein the living tumor-bearing subject is the individual patient to be treated with the bispecific cytotoxic lymphocyte or macrophage-redirecting autoantibody.

* * * * *

SEQUENCE LISTING

<160> NUMBER OF SEQ ID NOS: 1

<210> SEQ ID NO 1
<211> LENGTH: 56
<212> TYPE: PRT
<213> ORGANISM: Streptococcal sp.

<400> SEQUENCE: 1

Met Thr Phe Lys Leu Ile Ile Asn Gly Lys Thr Leu Lys Gly Glu Ile
1               5                   10                  15

Thr Ile Glu Ala Val Asp Ala Ala Glu Ala Glu Lys Ile Phe Lys Gln
            20                  25                  30

Tyr Ala Asn Asp Tyr Gly Ile Asp Gly Glu Trp Thr Tyr Asp Asp Ala
        35                  40                  45

Thr Lys Thr Phe Thr Val Thr Glu
    50                  55